(12) United States Patent
Harman et al.

(10) Patent No.: US 9,370,573 B2
(45) Date of Patent: Jun. 21, 2016

(54) POLYAMIDE COMPOSITIONS FOR PERSONAL CARE

(75) Inventors: Nancy W. Harman, Savannah, GA (US); George Miller, Savannah, GA (US); Thomas Fontana, Fleming Island, FL (US); Neal Kerckhoff, Tallahassee, FL (US); Jason Rothouse, Savannah, GA (US); Ramachandra Shastry, Dayton, NJ (US)

(73) Assignee: CRODA INTERNATIONAL PLC, East Yorkshire (GB)

( * ) Notice: Subject to any disclaimer, the term of this patent is extended or adjusted under 35 U.S.C. 154(b) by 0 days.

(21) Appl. No.: 14/342,886

(22) PCT Filed: Sep. 7, 2012

(86) PCT No.: PCT/US2012/054320
§ 371 (c)(1),
(2), (4) Date: Apr. 16, 2014

(87) PCT Pub. No.: WO2013/036878
PCT Pub. Date: Mar. 14, 2013

(65) Prior Publication Data
US 2014/0212363 A1    Jul. 31, 2014

Related U.S. Application Data

(60) Provisional application No. 61/532,913, filed on Sep. 9, 2011, provisional application No. 61/533,931, filed on Sep. 13, 2011.

(51) Int. Cl.
| | | |
|---|---|---|
| A61K 8/88 | (2006.01) | |
| A61Q 17/00 | (2006.01) | |
| C08G 69/00 | (2006.01) | |
| A61K 47/34 | (2006.01) | |
| C08G 69/34 | (2006.01) | |
| C08L 77/08 | (2006.01) | |
| C08G 69/26 | (2006.01) | |
| A61K 8/34 | (2006.01) | |
| A61Q 17/04 | (2006.01) | |
| A61Q 5/06 | (2006.01) | |
| A61Q 5/12 | (2006.01) | |
| A61Q 13/00 | (2006.01) | |
| A61Q 15/00 | (2006.01) | |

(52) U.S. Cl.
CPC . *A61K 47/34* (2013.01); *A61K 8/34* (2013.01); *A61K 8/88* (2013.01); *A61Q 5/06* (2013.01); *A61Q 5/12* (2013.01); *A61Q 13/00* (2013.01); *A61Q 15/00* (2013.01); *A61Q 17/04* (2013.01); *C08G 69/265* (2013.01); *C08G 69/34* (2013.01); *C08L 77/08* (2013.01)

(58) Field of Classification Search
CPC ....... A61Q 17/04; A61Q 13/00; A61Q 15/00; A61Q 5/06; A61Q 5/12; A61K 47/34; A61K 8/34; A61K 8/88; C08G 69/265; C08G 69/34; C08G 77/08
See application file for complete search history.

(56) References Cited

U.S. PATENT DOCUMENTS

| | | |
|---|---|---|
| 3,157,681 A | 11/1964 | Fischer et al. |
| 3,895,104 A | 7/1975 | Karg |
| 4,066,585 A * | 1/1978 | Schepp et al. ................ 524/279 |
| 4,514,540 A * | 4/1985 | Peck ............................ 524/514 |
| 4,571,267 A | 2/1986 | Drawert et al. |
| 4,668,765 A | 5/1987 | Drawert et al. |
| 4,731,242 A | 3/1988 | Palinczar |
| 5,330,565 A * | 7/1994 | Saitoh et al. .................. 523/102 |
| 5,500,209 A | 3/1996 | Ross et al. |
| 5,783,657 A | 7/1998 | Pavlin et al. |
| 6,268,466 B1 | 7/2001 | MacQueen et al. |
| 6,322,269 B1 | 11/2001 | Witz et al. |
| 6,395,269 B1 | 5/2002 | Fuller et al. |
| 6,399,713 B1 | 6/2002 | MacQueen et al. |
| 6,503,522 B2 | 1/2003 | Lawson et al. |
| 6,552,160 B2 | 4/2003 | Pavlin |
| 6,960,339 B1 | 11/2005 | Ferrari |
| 7,253,249 B2 | 8/2007 | Pavlin |
| 7,744,857 B2 | 6/2010 | Beachy et al. |

(Continued)

FOREIGN PATENT DOCUMENTS

| | | |
|---|---|---|
| GB | 1243552 | 8/1971 |
| WO | 2004093837 | 11/2004 |
| WO | WO 2011/047940 | 4/2011 |

OTHER PUBLICATIONS

International Search Report of PCT/US2012/054320, Issued Jan. 18, 2013.
Extended European Search Report of EP 12830251.0-1458, Issued Apr. 23, 2015.
Taiwan Examination Report and Search Report dated Feb. 5, 2016 for Taiwan Application No. 101132975.

*Primary Examiner* — Abigail Fisher
(74) *Attorney, Agent, or Firm* — RatnerPrestia

(57) ABSTRACT

Polyamide compositions useful for personal care are disclosed, including film-forming concentrates and emulsions. Ethanol-based concentrates comprise a hydrophobic polyamide, which comprises a reaction product of either (a) a dimerized fatty acid, at least one C2-C4 carboxylic acid, and a polyamine component comprising ethylenediamine and 1 to 30 eq. % of one or more di- or triamines; or (b) a dimerized fatty acid, at least 50 wt. % of a C16-C22 unsaturated carboxylic acid, and at least one C2-C6 diamine. Personal care applications for the concentrates, including continuous sunscreens, fragrant body sprays or splashes, anti-acne medications, are included. Water-in-oil emulsions comprising the hydrophobic polyamides are storage-stable and provide water-resistant SPF for products such as sunscreens and body lotions.

29 Claims, 5 Drawing Sheets

(56) References Cited

U.S. PATENT DOCUMENTS

| | | |
|---|---|---|
| 7,989,002 B2 | 8/2011 | Shah et al. |
| 2002/0127192 A1 | 9/2002 | Murphy et al. |
| 2003/0007940 A1 | 1/2003 | Wang et al. |
| 2006/0292095 A1 | 12/2006 | Biatry et al. |
| 2009/0016971 A1 | 1/2009 | Gaudry et al. |
| 2009/0035234 A1 | 2/2009 | Cunningham et al. |
| 2009/0324506 A1 | 12/2009 | Seidling et al. |
| 2009/0324659 A1 | 12/2009 | Polonka et al. |
| 2010/0272657 A1 | 10/2010 | He et al. |
| 2010/0310481 A1 | 12/2010 | Chevalier et al. |
| 2012/0204896 A1 | 8/2012 | Schweinsberg et al. |

* cited by examiner

POLYAMIDE COMPOSITIONS FOR PERSONAL CARE

This application is the U.S. National Phase application of PCT International Application No. PCT/US2012/054320, filed Sep. 7, 2012, which claims priority of U.S. Provisional Application No. 61/532,913, filed Sep. 9, 2011 and U.S. Provisional Application No. 61/533,931, filed Sep. 13, 2011, the disclosures of which are incorporated herein by reference in their entireties for all purposes.

FIELD OF THE INVENTION

The invention relates to compositions useful for personal care and other applications, and particularly to polyamide-containing concentrates and emulsions.

BACKGROUND OF THE INVENTION

Anhydrous sprays for personal care have become popular in recent years because they are easy to apply, go on clear, and require no rubbing to distribute over the skin. Mast personal care sprays use ethanol as a diluent. Ethanol-based continuous sunscreen sprays, although known in some form since the early 1970s (see, e.g., U.S. Pat. No. 3,895,104), are relatively new to the market. Because consumers like using them, such sprays have increased overall use of sunscreens and reduced incidences of sunburn and UVA exposure. However, existing formulations can have drawbacks, such as skin tightening, odor or limited durability on the skin; such drawbacks are attributed to film-forming polymers in used in sprays.

Polyamides and other synthetic polymers have been used as film-formers for personal care uses, including, for instance, sunscreen lotions. However, since the available polyamides have low compatibility with ethanol, they have not been used for anhydrous ethanol sprays. In addition, many polyamides used in personal care are gellant materials, and do not have desirable durability or skin feel, without additional formulation ingredients.

The film-forming polymer in an ethanol-based personal care application is critical. Often, there are few other components in the formulation. The film-farmer must bind active components (e.g., sunscreen actives) and secure them to the skin while providing good resistance to sweat or water. Moreover, consumers demand products that are tack-free, non-oily, non-tightening, and have good skin feel, and these properties all depend on the film-former.

Current commercial ethanol-based sunscreens in the U.S. typically include 1 to 5 wt. % of an acrylates/octylacrylamide copolymer, typically an acrylic resin from AkzoNobel known as Dermacryl® 79 (see, e.g., U.S. Pat. No. 6,322,776). Such sunscreen formulations can also include other film formers such as dimethicone polymers or other skin protectants (see, e.g., U.S. Pat. Appl. Nos. 2009/0035234 and 2009/0324506). Other acrylate film formers have been described (see, e.g., U.S. Pat. Nos. 4,731,242 and 6,395,269). Acrylates/octylacrylamide copolymer resin generally meets the needs for the film former, as it secures sunscreen actives and provides reasonably good water resistance, but it has limitations with respect to skin feel and related properties, as described above. In addition, Acrylates/octylacrylamide copolymer resin films may shrink slightly when applied from alcohol, giving a feeling of skin tightening. When an ethanol-based spray is applied, the ethanol quickly evaporates, and the resin rapidly forms a continuous film layer on the skin. Panels evaluating ethanol-based sunscreens (including those containing the acrylate-based film formers) continue to ask for products with lower tack, lower oiliness, and a softer, non-tightening skin feel.

Ultraviolet radiation can be damaging to skin. Immediate damage may be in the form of erythema. More long term is the concern of carcinomas or even melanoma. For these reasons, photoprotective agents, known as sunscreens, have been incorporated into cosmetic compositions.

Film-forming agents normally help to maintain a desirable sun protection factor (SPF) by securing sunscreen actives to the skin and imparting sweat and water resistance, thereby allowing the sunscreen actives to do their job under challenging conditions. Because sunscreen actives are expensive, any film former that can minimize the amount of sunscreen actives necessary to achieve a targeted SPF rating is desirable. Film-forming agents that not only maintain but actually enhance SPF in an ethanol-based personal care product while also providing desirable skin feel are needed.

U.S. Pat. Appl. Publ. No. 2010/0310481 teaches compositions comprising a hydrocarbon oil, a UV screening agent, a $C_1$-$C_3$ monoalcohol, and a lipophilic polyamide. The applicants teach that the kinds of lipophilic polyamides commonly used for sunscreen emulsions are not suitable for use in anhydrous, ethanol-based formulations. The exemplary formulations include 33 wt. % of capric/capyrlic triglyceride, 13 wt. % of a $C_{12}$-$C_{15}$ alkyl benzoate, and 6 wt. % of a particular polyamide resin; the description teaches that a wide variety of lipophilic polyamides are suitable. However, our own work indicates that many of the listed polyamides are incompatible with ethanol, particularly at low polyamide concentrations (e.g., 1-5 wt. %), and are therefore unsuitable for use in a continuous sunscreen spray.

A variety of polyamides and copolymers are well-known gellants for personal care, cosmetics, and air freshening (see, e.g., U.S. Pat. Nos. 6,268,466; 6,399,713; and 5,783,657). For additional examples, see U.S. Pat. Nos. 6,503,522; 6,960,339; and 7,989,002 and U.S. Pat. Appl. Publ. Nos. 2002/0127192 and 2006/0292095 (lipsticks or cosmetics); U.S. Pat. Nos. 5,500,209 and 7,744,857 (deodorants, antiperspirants); and U.S. Pat. Nos. 6,552,160 and 7,253,249 (candles and air fresheners). U.S. Pat. Appl. Publ. No. 2009/0324659 describes sunscreen composite particles useful for cosmetics that may comprise a polyoxyalkylene polyamide resin such as Polyamide-3. Ethanol-based sunscreens that contain Polyamide-3 (as Sylvasol™ 80 specialty polymer, product of Arizona Chemical) are also described.

U.S. Pat. Appl. Publ. No. 2010/0272657 teaches use of an amine additive to neutralize acid groups of a film-forming polymer, thereby improving the SPF rating. However, polyamides are not used as the film-forming polymer.

Emulsions useful as body lotions, sunscreens, and the like continue to be mainstays in the personal care arena. Formulators need emulsions that have good shelf life and maintain an acceptable SPF rating even after exposure to sweat or water immersion.

A need remains to identify improved compositions for use in body lotions, sunscreen lotions, continuous spray sunscreens, body splashes, and other personal care products. Of particular interest are ethanol-compatible, film-forming polymers that can give a clear solution with sunscreens, fragrances, cosmetics, medications, or other active components, and can be applied to the skin, hair, or scalp as a spray to leave a water-resistant film.

Preferably, the film-forming polymer would enhance the formulation SPF to minimize the amount of sunscreen actives needed. Many sunscreen agents are greasy or sticky when applied to the skin. Current polymers in sunscreen sprays cannot be used in amounts to overcome these properties and still provide a good film when sprayed onto skin. Consumers would like sunscreens in which the film-forming polymer can overcome greasy or sticky characteristics of sunscreen actives and still have good skin feel. Consumers also would like formulations that did not tighten the skin as they dry. In addition, formulators would prefer a film-forming polymer that would boost SPF so that less of the sunscreen active would be required to get an equivalent SPF.

A valuable ethanol-based composition would be homogeneous, sprayable using a valve-on-bag spray can or pump, and provide a continuous, even film at skin protection factors up to SPF 100. Ideally, the formulation would delight customers with low tack, low oiliness, and a soft, non-tightening skin feel when compared with commercially available ethanol-based sprays. Additionally, improved emulsions having good stability, acceptable SPF ratings, and good water resistance are always in demand.

SUMMARY OF THE INVENTION

Our invention relates, in part, to film-forming concentrates of certain hydrophobic polyamides that are suitable for use in personal care products. The concentrates comprise 50 to 99.9 wt. % of ethanol and 0.1 to 50 wt. % of a certain hydrophobic polyamide. In one aspect, the polyamide comprises a reaction product of a dimerized fatty acid, at least one $C_2$-$C_4$ carboxylic acid, and a polyamine component comprising ethylenediamine and 1 to 30 eq. % of one or more di- or triamines. In another aspect, the polyamide comprises a reaction product of a dimerized fatty acid, at least 50 wt. % of a $C_{16}$-$C_{22}$ unsaturated carboxylic acid, and at least one $C_2$-$C_6$ diamine. unexpectedly found these particular polyamides formed films on skin and textiles to deliver active ingredients or fragrances when applied from ethanol spray or emulsions.

The invention also relates to personal care applications for the concentrates of such polyamides, including continuous sunscreens, fragrant body sprays or splashes, anti-acne medications, and the like. The concentrates can also be used to coat fabrics with insecticides, water repellants, stain repellants, disinfectants, deodorizers, antistatic agents, or other actives.

Methods which comprise formulating an ethanol-based personal care product having boosted SPF are also included. The polyamides of this invention do not disperse in ethanol easily at room temperature. Therefore both room temperature and elevated temperature methods are provided. The personal care product contains one or more of certain hydrophobic polyamides. The polyamide is either (a) a reaction product of a dimerized fatty acid, at least one $C_2$-$C_4$ carboxylic acid, and a polyamine component comprising ethylenediamine and 1 to 30 eq. % of one or more di- or triamines; or (b) a reaction product of a dimerized fatty acid, at least 50 wt. % of a $C_{16}$-$C_{22}$ unsaturated carboxylic acid, and at least one $C_2$-$C_6$ diamine. In either case, the polyamide is used in an amount effective to boost the SPF of the personal care product by at least 50%, compared with the SPF of a similar product formulated in the absence of the polyamide.

In another aspect, the invention relates to a method for making a continuous sunscreen spray. The method comprises (a) combining one or more sunscreen actives with ethanol at a temperature within the range of 20° C. to 50° C. to form a first mixture; and (b) combining the first mixture with a hydrophobic polyamide at a temperature within the range of 15° C. to 40° C. to give the continuous sunscreen spray. Preferably, the polyamide is as described above. We unexpectedly discovered that the hydrophobic polyamide can be formulated into the continuous sunscreen spray even at room temperature when this order of addition is used.

In yet another aspect, the invention relates to a method for making a continuous sunscreen spray. The method comprises combining a hydrophobic polyamide, selected from certain polyamides, with ethanol and at least one sunscreen active in the presence of at least 2 wt. %, based on the amount of sunscreen spray, of a fatty alcohol.

The invention includes emulsions comprising a hydrophobic polyamide, selected from certain polyamides. Water-in-oil emulsions comprise: (a) a continuous phase comprising 30 to 90 wt. % of water, based on the amount of emulsion; and (b) a discontinuous phase comprising at least one oil component and a hydrophobic polyamide. Oil-in-water emulsions are also included. These comprise a discontinuous phase comprising water and a continuous phase comprising at least one oil component and a hydrophobic polyamide selected from certain polyamides.

In order to show one of the benefits of our invention, we developed a method of comparing skin tightening effects of film-forming materials in cosmetic formulations. The method quantifies skin tightening qualities of a product by measuring forces of contraction or expansion of a skin substitute, mounted on a substrate support system. Contractile forces result from the nature of the film that is formed on the substrate. A substrate support system holds the skin substitute sample in tension, and attaches to a load cell. The load cell is part of an instrument, such as an Instron® tensile testing machine, that measures force as a function of time. When a formulation is applied to a skin substitute that has been mounted in a substrate support system, it causes the skin substitute to relax or tighten. The relaxation or tightening in the skin substitute results in an increase or decrease in tension force, detected by the load cell and transmitted to the instrument and translated to a measurement of force. Measurements of contractile force are taken as a function of time to quantify the tightening or relaxing effect of the skin care formulation.

We surprisingly found that the ethanol-based concentrates of certain hydrophobic polyamides, when applied as a spray at appropriate dilution, provide water-resistant films that secures sunscreens, fragrances, medications, cosmetics, and other active components while boosting SPF, and delivering improved skin feel properties, including low tack, low oiliness, and reduced skin tightness. Emulsions of certain hydrophobic polyamides of the invention impart good stability, acceptable SPF ratings, and good water resistance to body lotions, sunscreens, and other similar personal care products.

DETAILED DESCRIPTION OF THE INVENTION

Figure 1:
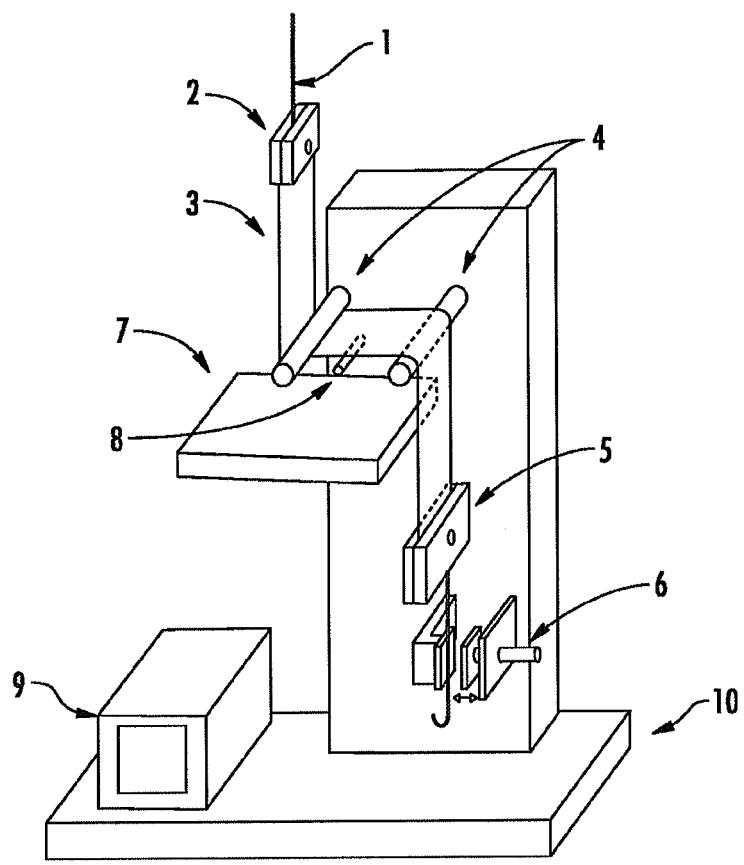
FIG. 1 illustrates a substrate support used for evaluating skin tightening, using a tensile testing machine, such as an Instron® tester.

In general, the invention relates to polyamide compositions useful in making products for the personal care and other industries. In one aspect, the invention relates to ethanol-based film-forming concentrates of certain hydrophobic polyamides for use in personal care or fabric coating. We first consider ethanol-based concentrates useful for personal care.

Personal care products that can be applied to the skin, hair, or scalp as an ethanol-based spray comprise ethanol, active components, and a film former. In contrast to existing commercial products, which normally use an acrylic film former, the inventive concentrates comprise a particular variety of hydrophobic polyamide. That is, not all hydrophobic polyamides are suitable for use. We found through a series of solubility, in vitro, and in vivo tests that particular hydrophobic polyamides provide not only good solubility characteristics in ethanol, but also improved skin feel properties that consumers prefer.

In one aspect of the invention, the hydrophobic polyamide is a reaction product of a dimerized fatty acid, at least one $C_2$-$C_4$ carboxylic acid, and a polyamine component. The polyamine component comprises ethylenediamine and 1 to 30 eq. % of one or more di- or triamines, preferably hexamethylene diamine. In another aspect, the polyamide is a reaction product of a dimerized fatty acid, at least 50 wt. % of a $C_{16}$-$C_{22}$ unsaturated carboxylic acid, and at least one $C_2$-$C_6$ diamine. These two groups of polyamides each form clear dispersions or solutions in ethanol, and, when applied to the skin, form water-resistant, rub-resistant films with good skin feel and minimal tightening.

Dimerized fatty acids (also called "dimer acids") are complex products made by polymerizing an unsaturated fatty acid according to methods that are well known in the art. See, e.g., U.S. Pat. No. 3,157,681, the teachings of which are incorporated herein by reference, and *Naval Stores—Production, Chemistry and Utilization*, D. F. Zinkel and J. Russell (eds.), Pulp. Chem. Assoc. Inc. (1989), Chapter 23. Suitable dimerized fatty acids are mostly dibasic acids with a smaller proportion of monomer acid, trimer fatty acids, and possibly some higher polymers. Preferred dimer acids are liquids having an acid number within the range of 180 to 200 mg KOH/g, preferably from 185 to 200 mg KOH/g. Dimer acids can be synthesized, but they are also commercially available. Examples include the Unidyme® series of dimer acids, products of Arizona Chemical. Suitable dimer acids include once-distilled (or "single pass") dimer acids, which in some instances may contain about 80% dimer acids, about 17% trimer fatty acids, and about 3% monomer fatty acid content. Suitable dimer fatty acids also include twice-distilled (or "double pass") dimer fatty acids, which have higher dimer acid contents, such as 93% or more dimer fatty acids, in some instances about 95% dimer fatty acids and about 5% trimer fatty acids.

The dimerized fatty acid can be hydrogenated if desired prior to using it as a reactant for making the hydrophobic polyamide. Hydrogenation saturates carbon-carbon double bonds in the dimerized fatty acid, which helps to minimize color development in the polyamide resin. Polyamides B and Q in the examples below illustrate the utility of a hydrogenated dimer acid as a reactant.

The $C_2$-$C_4$ carboxylic acid is conveniently used to limit the molecular weight of the polyamide. Suitable carboxylic acids include acetic acid, propionic acid, n-butyric acid, isobutyric acid, or the like, and mixtures thereof. Preferably, acetic acid, propionic acid, or a mixture thereof is used. Most preferred is a mixture of acetic and propionic acids.

The polyamine component comprises ethylenediamine and from 1 to 30 eq. % of one or more diamines or triamines, preferably hexamethylene diamine, diethylenetriamine, or mixtures thereof. Ethylenediamine may be the major polyamine component, when used in an amount within the range of 70 to 99 eq. % based on the combined amounts of ethylenediamine and one or more additional di- or triamines. Suitable di- and triamines also include, e.g., 1,3-diaminopropane, 1,4-diaminobutane, and the like. In preferred polyamides, the equivalent ratio of ethylenediamine to the additional di- or triamine ranges from 3:1 to 100:1, more preferably from 4:1 to 20:1, most preferably from 5:1 to 10:1.

When the polyamide comprises a reaction product of a dimerized fatty acid, at least 50 wt. % of a $C_{16}$-$C_{22}$ unsaturated carboxylic acid, and at least one $C_2$-$C_6$ diamine, the $C_2$-$C_6$ diamine is preferably ethylenediamine. Suitable $C_{16}$-$C_{22}$ unsaturated carboxylic acids are monocarboxylic acids that have at least one carbon-carbon double bond. Examples include palmitoleic acid, oleic acid, ricinoleic acid, linoleic acid, linolenic acid, gadoleic acid, erucic acid, and the like. Oleic acid is particularly preferred. One preferred polyamide of this type is a reaction product of 25 to 35 wt. % of the dimerized fatty acid, 55 to 65 wt. % of a $C_{16}$-$C_{22}$ unsaturated carboxylic acid (especially oleic acid), and 9 to 10 wt. % of ethylenediamine.

The hydrophobic polyamides of this invention are prepared using well-known condensation polymerization methods. In one convenient approach, a one-step procedure is used. All of the reactants (dimerized fatty acid, polyamines. $C_2$-$C_4$ carboxylic acid, and any catalyst) are simply combined and heated with good agitation at a temperature effective to induce condensation polymerization. Preferably, the temperature is within the range of 180° C. to 250° C., more preferably from 200° C. to 240° C. A catalyst is not required, but a mineral acid such as phosphoric acid or the like can be included if desired to accelerate the reaction. The reaction typically requires from 3 to 8 hours. Water of reaction is removed as the condensation proceeds. Vacuum or an inert-gas sparge can be used to assist in water removal. Progress of the reaction is conveniently monitored by measuring acid number, amine number, or both according to well-known methods. The general procedure given below for the preparation of the hydrophobic polyamides is illustrative.

In general, it is desirable to use substantially equivalent molar amounts of amine and carboxylic acid reactants to prepare the hydrophobic polyamide. In some cases, particularly for personal care applications, it may be preferred to have a slight excess of the carboxylic acid such that the amine number is measurably lower than the acid number.

Generally, the polyamides useful in this invention are made from a reaction mixture comprising 70 to 90 wt. % of the dimer acid, 2 to 15 wt. % of the $C_2$-$C_4$ carboxylic acid, and 10 to 20 wt. % of the polyamine component. More preferably, the reaction mixture comprises 75 to 85 wt. % of the dimer acid, 5 to 10 wt. % of the $C_2$-$C_4$ carboxylic acid, and 10 to 15 wt. % of the polyamine component.

Preferred polyamides have a number average molecular weight, conveniently determined by gel permeation chromatography, within the range of 1000 to 5000, more preferably from 1200 to 4000, and most preferably from 1500 to 3500. Preferred polyamides have an acid number less than 10 mg KOH/g and an amine number less than 5 mg KOH/g. Preferred polyamides have a softening point (as measured using the ring and ball method ASTM E28-99) within the range of 120° C. to 140° C., more preferably 122° C. to 138° C.

As the examples below show, not all hydrophobic polyamides are compatible with ethanol. Some resins are soluble in n-propyl alcohol but give a hazy mixture at 4 wt. % resin in ethanol (see, e.g., Polyamide P). Such polyamides might be less preferred for use in sprayable personal care applications, depending on consumer preference for a spray that goes on clear. Moreover, even hydrophobic polyamide resins that are compatible with ethanol can still fail a skin feel test (e.g., Polyamides L and M). Polyamides L and M comprise more than 30 eq. % of hexamethylene diamine as the polyamine component; their ratio of ethylenediamine to hexamethylene diamine equivalents is in the range of 1.5:1 to 2:1.

The film-forming concentrates are mixtures of ethanol and a hydrophobic polyamide. Suitable concentrates comprise 50 to 99.9 wt. % of ethanol and 0.1 to 50 wt. % of the polyamide. Preferred concentrates comprise 90 to 99 wt. % of ethanol and 1 to 10 wt. % of the polyamide. Most preferred are concentrates comprising 95 to 99 wt. % of ethanol and 1 to 5 Rt. % of the polyamide. Preferably, the ethanol used is "specialty denatured ethanol" (SDA). 190-200 proof, (e.g., ethanol SDA-40B or ethanol SD-40), which is sold specifically for use in personal care applications.

The film-forming concentrates of the invention are clear and remain so even when diluted with ethanol to the concentrations normally used in a spray application. Preferably, the polyamide, when mixed with 200 proof ethanol, exhibits a cloud point, if any, below 15 wt. % polyamide, more preferably below 10 wt. %, and most preferably below 5 wt. %. In general, the higher the concentration of ethanol, the more difficult it is to maintain a clear concentrate.

Film-forming concentrates of the invention are valuable for formulating a variety of personal care products that can be applied as an ethanol-based spray to the skin, hair, or scalp. The products include, for example, continuous sunscreen sprays, fragrant body sprays or splashes, anti-acne sprays, hair-growth stimulants, hair styling agents, hair conditioners, skin toners, antiseptics, deodorants, antiperspirants, moisturizers, anti-itch agents, over-the-counter products, topical medications or pharmaceuticals, and the like. The inventive concentrates afford improvements in skin feel properties compared with commercially available alternatives.

In one aspect, our invention relates to a continuous sunscreen spray having improved skin feel. The spray comprises an inventive ethanol-based concentrate of hydrophobic polyamide, as described above, and at least one sunscreen active component. The concentrate with the sunscreen ingredient is formulated into a spray by diluting with ethanol to give a hydrophobic polyamide content within the range of 0.2 to 8 wt. %, more preferably from 1 to 6 wt. %, and most preferably from 1.5 to 4 wt. %. Surprisingly, we have found that adding more hydrophobic polyamide of the invention up to about 5 wt. % increases the SPF of such sunscreen formulations, while retaining good film-forming properties, good skin feel, and water resistance. Higher amounts of hydrophobic polyamide appear to retain SPF improvement, giving formulators flexibility in how much hydrophobic polyamides to use.

Suitable sunscreen active components are well known in the art. A typical sunscreen spray will include multiple sunscreen active components that absorb different kinds (UV-A, UV-B) or wavelength ranges of ultraviolet radiation. Sunscreen actives generally absorb or block infrared rays and/or UV rays in the wavelength range from 290 to 420 nm.

Suitable sunscreen actives include, for example: p-aminobenzoic acid derivatives (e.g., ethyl p-aminobenzoate, ethyl dihydroxypropyl p-aminobenzoate); salicylic acid derivatives (homosalate, ethylhexyl salicylate), cinnamic acid derivatives (ethylhexyl methoxycinnamate, cinoxate), benzophenones or aminobenzophenones (benzophenone-1, benzophenone-3), anthranilic acid derivatives (methyl anthranilate), dibenzoylmethane derivatives (4-isopropyldibenzoylmethane, butyl methoxydibenzoylmethane), β,β-diphenylacrylate derivatives (octocrylene, etocrylene), benzylidene camphor derivatives (3-benzylidene camphor, methylbenzylidene camphor), phenylbenzimidazole derivatives, benzotriazole derivatives. triazine derivatives (ethylhexyl triazone), bisresorcinyltriazines, imidazoline derivatives, benzalmalonate derivatives, 4,4-diarylbutadiene derivatives. benzoxazole derivatives, merocyanines, and their mixtures.

Preferred sunscreen actives include butyl methoxydibenzoylmethane, n-hexyl 2-(4-diethylamino-2-hydroxybenzoyl) benzoate, homosalate, ethylhexyl salicylate, ethylhexyl methoxycinnamate, octocrylene, ethylhexyl triazone, 2,4-bis (n-butyl 4'-aminobenzoate)-6-(aminopropyl-trisiloxane)-s-triazine, octyl 5-N,N-diethylamino-2-phenylsulfonyl-2,4-pentadienoate, benzophenone-3, drometriazole trisiloxane, and bis-ethylhexyloxyphenol methoxymethyl triazine.

Particularly preferred sunscreen sprays contain one or more of butyl methoxydibenzoylmethane, homosalate, ethylhexyl salicylate. ethylhexyl methoxycinnamate, and octocrylene.

Other suitable sunscreen actives are described in U.S. Pat. Nos. 7,744,911 and 5,000,937, and in U.S. Pat. Appl. Publ. Nos. 2009/0035234 and 2010/0310481, the teachings of which are incorporated herein by reference.

The amount of sunscreen actives in the spray is usually adjusted to achieve a targeted skin protection factor, e.g., SPF 8, 15, 30, 45, 70 or 100. Generally, the amount used will be within the range of 0.1 to 25 wt. %, more preferably 1 to 15 wt. %, based on the amount of fully formulated sunscreen spray.

A sunscreen spray can include other components in addition to the ethanol, hydrophobic polyamide, and sunscreen actives. For instance, the spray can include anti-oxidants, finely-dispersed light-blocking micro- or nano-pigments, emollients, carriers, and the like. Preferred sunscreen sprays include glycerin, typically 1-4 wt. % based on the amount of fully formulated spray, which can enhance skin feel properties.

In one preferred method of this invention, the continuous sunscreen spray is prepared by adding a warm, homogeneous mixture of sunscreen active components to a cool (e.g., room-temperature) solution of ethanol and hydrophobic polyamide. Examples 1 and 5 illustrate this method. Depending on the particular sunscreen actives and polyamide, all of the components might simply be combined at room temperature (see Example 4). These "room temperature" methods are generally preferred by sunscreen formulators, who would prefer to add an ethanol solution containing polyamide directly to a mixture of the sunscreen actives and ethanol at room temperature. Formulators would prefer not to heat ethanol or the sunscreen actives to temperatures greater than 50° C. As Table 3 below shows, the room temperature methods are particularly useful in formulating continuous sunscreens using Polyamides A, B, and C.

In an alternative approach ("the hot process"), illustrated below in Example 3, the sunscreen actives and hydrophobic polyamide are heated to a temperature greater than 50° C. preferably from 60° C. to 100° C., to solubilize the polyamide with the actives. After cooling, the mixture is then combined with ethanol to give the continuous sunscreen spray formulation. Certain polyamide resins, e.g. Polyamide D, are preferably formulated into continuous ethanol-based sunscreens using the hot process.

In another aspect, the invention relates to fragrant body sprays and splashes comprising the inventive concentrates.

These formulations include, in addition to ethanol and the hydrophobic polyamide, at least one fragrance component. Preferably, the fragrant body spray or splash also includes glycerin, propylene glycol, or both. Additional components can include skin protectants, antioxidants, sunscreen actives, or other components. Example 6 below illustrates a suitable formulation.

The invention includes methods which comprise formulating an ethanol-based personal care product having boosted SPF. The personal care product contains a hydrophobic polyamide. In one aspect, the polyamide comprises a reaction product of a dimerized fatty acid, at least one $C_2$-$C_4$ carboxylic acid, and a polyamine component comprising ethylenediamine and 1 to 30 eq. % of a di- or polyamine. The polyamide can also comprise a reaction product of a dimerized fatty acid, at least 50 wt. % of a $C_{16}$-$C_{22}$ unsaturated carboxylic acid, and at least one $C_2$-$C_6$ diamine. Both of these polyamides have been described earlier. In either case, the polyamide is used in an amount effective to boost the sun protection factor (SPF) of the personal care product by at least 50%, preferably by at least 75%, more preferably by at least 150%, compared with that of a similar product formulated in the absence of the polyamide.

As shown in Table 7, we surprisingly found that increasing the concentration of Polyamide A generally enhances the SPF value. This attribute of the polyamide is valuable because it allows formulators to reduce the amount of sunscreen actives needed to achieve a desired SPF rating. The boost in SPF is apparent at relatively low levels of film-forming agent. Thus, we found that SPF could be increased up to 160% in an SPF 30 formulation and more than 250% in an SPF 50+ formulation by using the inventive polyamides. Although spreadability of the formulation can become an issue at relatively high polymer loads, excellent results are available at 4-6 wt. % of the polyamide, an amount typically used in personal care applications such as ethanol-based sunscreen sprays, body sprays, fragrance sprays, and other similar applications.

In another aspect, the invention relates to a method for making a continuous sunscreen spray. The method comprises two steps. First, one or more sunscreen actives are combined with ethanol at a temperature within the range of 20° C. to 50° C., preferably 20° C. to 40° C., more preferably 20° C. to 30° C., most preferably room temperature, to form a first mixture. When two or more sunscreen actives are present, they may be combined in advance, preferably by gentle warming, prior to combination with ethanol. The first mixture preferably further comprises glycerin. The first mixture is then combined with a hydrophobic polyamide at a temperature within the range of 15° C. to 40° C., preferably 20° C. to 35° C., more preferably 20° C. to 30° C., most preferably room temperature, to give the continuous sunscreen spray. Suitable polyamides and sunscreen actives have already been described. Optionally, the spray further comprises a compatibilizer, preferably a fatty alcohol as described further below.

We surprisingly found a method of improving an otherwise "finished" ethanol-based continuous sunscreen spray formulation by directly adding the hydrophobic polyamides of this invention, even at room temperature, to give a homogeneous solution. In the inventive method, sunscreen actives are typically warmed and combined with ethanol, and the polyamide is added thereafter. Surprisingly, the hydrophobic polyamide dissolves in the ethanol/sunscreen actives mixture even at room temperature, typically within an hour. This method avoids any need to heat ethanol with a normally-solid polyamide to generate an ethanol/polyamide solution into which sunscreen actives can be added. The method also avoids any need to ship or store a blend of ethanol and polyamide. Examples 9 and 10 below are illustrative (see also Table 8).

In some instances, it may be desirable to include a compatibilizer in polyamide compositions of the invention. For example, a compatibilizer can be used to help accelerate formation of homogeneous, ethanol-based concentrates containing the hydrophobic polyamides of the invention. Preferred compatibilizers are fatty alcohols, i.e., compounds or mixtures of compounds having at least one $C_6$-$C_{30}$ saturated or unsaturated, linear or branched, hydrocarbyl group and at least one hydroxyl group. Preferred compatibilizers are those already known to have value for use in personal care applications. Suitable compatibilizers include, for example, 2-octyldodecanol, oleyl alcohol, castor oil, isostearyl alcohol, 2-ethylhexyl glycerin, and the like, and mixtures thereof. See Examples 13 and 14 below, which illustrate the use of 2-octyldodecanol in the preparation of body lotions and sport sunscreens.

In another inventive method, a continuous sunscreen spray is made. The method comprises combining a hydrophobic polyamide with ethanol and at least one sunscreen active in the presence of at least 2 wt. %, preferably from 2 to 8 wt. %, more preferably from 3 to 7 wt. %, based on the amount of sunscreen spray, of a fatty alcohol. Preferred fatty alcohols are those described above. 2-Octyldodecanol is particularly preferred. Example 11 below illustrates this method. Comparative Example 12 shows that the method is more effective when at least 2 wt. % of the fatty alcohol is used.

The film-forming concentrates of certain polyamides are also suitable for compositions for use in coating fabrics. The concentrates comprise 50 to 99.9 wt. % of ethanol and 0.1 to 50 wt. % of a hydrophobic polyamide selected from certain polyamides. In one aspect, the polyamide comprises a reaction product of a dimerized fatty acid, at least one $C_2$-$C_4$ carboxylic acid, and a polyamine component comprising ethylenediamine and 1 to 30 eq. % of a di- or triamine. Suitable polyamides of this type have already been described above. In another aspect, the polyamide comprises a reaction product of a dimerized fatty acid, at least 50 wt. % of a $C_{16}$-$C_{22}$ unsaturated carboxylic acid, and at least one $C_2$-$C_6$ diamine. Again, these polyamides are also described above. The fabric coating compositions preferably include one or more active materials such as insecticides, water repellants, stain repellants, disinfectants, deodorizers, antistatic agents, and the like, and mixtures thereof. The compositions should have particular value for outdoor use, e.g., for treating tents, outerwear backpacks, or the like.

The hydrophobic polyamides of our invention may also be formed into emulsions of certain film-forming hydrophobic polyamides and, surprisingly, retain their film-forming properties after drying. In one aspect, such an emulsion is an oil-in-water emulsion. The oil-in-water emulsions comprise continuous and discontinuous phases. The continuous phase comprises 30 to 90 wt. % water, based on the amount of emulsion. The discontinuous phase comprises at least one oil component and a polyamide selected from certain film-forming hydrophobic polyamides. Suitable polyamides have already been described. Preferably, the oil component comprises at least one sunscreen active.

In another aspect, the emulsion is a water-in-oil emulsion. In this case, the aqueous phase is discontinuous, and the continuous phase comprises at least one oil component and a hydrophobic polyamide. Water-in oil emulsions are common in the personal care industry in the form of creams or thick lotions. Again, the water-in-oil emulsions retain the water-resistance and film-forming properties of the hydrophobic polyamides.

The inventive emulsions are useful for formulating a wide variety of personal care products, including, for instance, fragrant body lotions, sport sunscreens, moisturizers, aftershave lotions, tanning lotions, shampoos. and hair conditioners. Examples of topical medical products include creams or lotions containing analgesics, acne medications, anesthetics, steroids (such as hydrocortisone), anti-bacterial, anti-fungal, deodorants, lice treatments, wart treatments, and the like. We found that the hydrophobic polyamides of this invention can be used to formulate homogeneous emulsions that have good stability and desirable viscosities. Significantly, the polyamides of this invention retain their film-forming properties to impart good skin feel and water resistance.

Example 13, below, shows how to formulate a long-lasting fragrant body lotion using Polyamide A. A sport sunscreen lotion based on an inventive oil-in-water emulsion is shown in Example 14. The lotion performs well in both in vitro testing (see Table 9) and in vivo testing (see Table 10) when compared with a similar formulation without the hydrophobic polyamide (Comparative Example 16). The in vivo results for the 80-minute "very water resistant" (VWR) test are particularly interesting, as the comparative SPF 50 lotion fails in four of five test subjects, while all five subjects pass when Polyamide A is present in the lotion (Table 10).

The following examples merely illustrate the invention. Those skilled in the art will recognize many variations that are within the spirit of the invention and scope of the claims.

Preparation of Hydrophobic Polyamides: General Procedure

The following method is used to prepare the polyamides used in the inventive and comparative examples.

The reactants listed in Tables 1 and 2 are combined and agitated to generate a homogeneous mixture. The reaction temperature is gradually increased to 220° C., and heating continues for 4-6 h while the water of reaction is removed. Progress of the reaction is monitored by periodically taking samples to analyze for acid number and/or amine number. Polyamides A-H, J, and K are used to make inventive compositions, while Polyamides L, M, N, P, and Q are used to make comparative compositions.

Ethanol Compatibility:

Polyamide resins are evaluated for their potential as film-formers for an ethanol-based continuous sunscreen spray. Ethanol SD-40 (200 proof, 48 g) and a polyamide resin (2.0 g) are combined and heated to reflux on a hot plate. After cooling, the mixtures are evaluated for clarity and compatibility or phase separation. Based on this screening test, Polyamides A-H and J-M give a clear solution and merit further evaluation, while Polyamides N, P, and Q are eliminated from further consideration because of incompatibility.

Skin Feel Testing:

Resins that provide a clear solution at 4% solids are evaluated for skin feel properties. Fully formulated SPF 30 and SPF 70 sunscreens containing 4.0 wt. % of the hydrophobic polyamide are prepared. The formulation for the SPF 70 sunscreen is shown in Example 1. Two separate trials are performed in which sunscreens are applied as a spray to the skin of five or six panel participants. The scores shown in Table 3 reflect an average of the panelists' ratings. Tightness on the skin, tack (or stickiness), and oiliness are rated on a scale of 1 to 5, with 1=best and 5=worst. The sunscreens are also evaluated for balling or flaking and for overall skin feel.

Overall, the panelists agreed that Polyamides A-D outperform sunscreens with acrylates/octylacrylamide copolymer, the commercial control, particularly in the important area of skin tightness. Polyamide L is eliminated from further consideration because the films ball up when the skin is rubbed following evaporation of the ethanol (see Table 3). Additional skin feel tests performed on Polyamides E-H and J also demonstrate excellent performance (see Table 1).

In Vitro Test Results

Ethanol-based sunscreen sprays (SPF 70) containing either Polyamide A or acrylates/octylacrylamide copolymer are applied to samples of "Vitro™ skin," a synthetic product having topography, pH, critical surface tension, and other properties resembling human skin. Skin tightening is evaluated using an Instron® instrument and measuring tightening force as a function of time. The formulation based on Polyamide A exhibits a reduced skin tightening effect when compared with an acrylates/octylacrylamide copolymer formulation in this test. Details of this test and more results appear below ("In Vitro Skin Tightening Study").

TABLE 1

Hydrophobic Polyamides for the Inventive Examples

| | Polyamide | | | | | | | | | |
|---|---|---|---|---|---|---|---|---|---|---|
| | A | B | C | D | E | F | G | H | J | K |
| Formulation (wt. %) | | | | | | | | | | |
| dimer acid, once distilled[1] | 81.8 | — | 81.8 | 30.4 | — | — | — | 57.5 | — | — |
| dimer acid, once distilled | — | — | — | — | — | — | — | 25.0 | — | — |
| dimer acid, twice distilled[2] | — | — | — | — | 81.7 | 80.6 | 80.3 | — | 80.3 | 80.7 |
| hydrogenated twice-distilled dimer acid | — | 81.7 | — | — | — | — | — | — | — | — |
| propionic acid | 2.2 | 2.2 | 2.2 | — | 2.2 | 2.2 | 1.7 | — | 2.2 | 1.7 |
| acetic acid | 3.5 | 3.5 | 3.2 | — | 3.5 | 3.4 | 3.8 | 6.0 | 3.4 | 3.8 |
| oleic acid | — | — | — | 60.2 | — | — | — | — | — | — |
| Sylfat ® FA-1 fatty acid[3] | — | — | — | — | — | — | — | 0.11 | — | — |
| ethylenediamine | 9.4 | 9.4 | 9.6 | 9.4 | 95 | 9.3 | 9.0 | 8.4 | 9.0 | 9.3 |
| hexamethylenediamine | 3.1 | 3.1 | 3.2 | — | 4.5 | 4.4 | 5.1 | — | 5.1 | 4.4 |
| diethylenetriamine | — | — | — | — | — | — | — | 3.1 | — | — |
| Equivalent ratio[4]: | 15 | 15 | 15 | N/A | 20 | 20 | 23 | 25 | 23 | 20 |
| Polyamide properties | | | | | | | | | | |
| Mn | 2570 | 2560 | 2720 | 1330 | 2780 | 3060 | 2780 | 2430 | 2730 | 2720 |
| Mw | 5830 | 5600 | 8440 | 1980 | 5870 | 6270 | 5910 | 6360 | 5880 | 5820 |
| acid # (mg KOH/g) | 5.9 | 5.6 | 2.0 | 5.6 | 5.8 | 5.1 | 5.6 | — | 3.8 | 3.6 |
| amine # (mg KOH/g) | 0.80 | 1.3 | 3.0 | 3.0 | 1.0 | 0.9 | 1.0 | — | 1.4 | 1.1 |
| softening pt, ° C.[5] | 138 | 138 | 126 | 121 | 127 | 131 | 130 | 123-33 | 124 | 124 |

TABLE 1-continued

Hydrophobic Polyamides for the Inventive Examples

| | Polyamide | | | | | | | | | |
|---|---|---|---|---|---|---|---|---|---|---|
| | A | B | C | D | E | F | G | H | J | K |
| Gardner color[6] | 5 | 2 | 6 | 4- | 5 | 7 | 7- | — | 7 | 7 |
| clarity (4 wt. % in EtOH) | clear | clear | clear | clear | clear | clear | clear | clear | clear | clear |
| skin feel[7] | E | G | G | E | E | E | E | E | E | — |
| in vitro SPF, static, 70 SPF | 66 | — | — | 53 | 66 | 58 | 61 | 63 | — | — |
| in vitro SPF, VWR, 70 SPF | — | — | — | — | — | 65 | 76 | 97 | — | — |

[1]Once-distilled dimer acid: ~80% dimer, 17% trimer acids.
[2]Twice-distilled dimer acid: ~95% dimer, ~5% trimer acids.
[3]Sylfat ® FA-1 fatty acid is a product of Arizona Chemical.
[4]Equivalent ratio calculated from (DETA + HMDA equivs.)/(DETA + HMDA + EDA equivs) × 100, where DETA = diethylenetriamine, HMDA = hexamethylenediamine, and EDA = ethylenediamine.
[5]Ring and ball method, Mettler instrument, ASTM E28-99.
[6]50% solution in 1-propanol.
[7]E = excellent; G = good.

TABLE 2

Hydrophobic Polyamides for the Comparative Examples

| Polyamide | L | M | N | P | Q |
|---|---|---|---|---|---|
| Formulation (wt. %) | | | | | |
| dimer acid, once distilled[1] | 81.3 | 78.3 | 80.0 | 60.4 | — |
| hydrogenated twice-distilled dimer acid | — | — | — | — | 70.0 |
| propionic acid | 5.2 | 7.0 | — | — | — |
| acetic acid | — | — | 7.9 | — | — |
| stearic acid | — | — | — | 18.8 | — |
| azelaic acid | — | — | — | — | 0.12 |
| oleic acid | — | — | — | 30.0 | — |
| Sylfat ® FA-1 fatty acid[3] | — | — | 0.10 | — | — |
| ethylenediamine | 6.0 | 6.1 | 12.0 | 9.7 | 9.2 |
| hexamethylenediamine | 6.0 | 7.6 | — | — | 1.8 |
| diethylenetriamine | 1.6 | 1.0 | — | — | — |
| Equivalent ratio[4]: | 43 | 44 | N/A | N/A | N/A |
| Properties | | | | | |
| Mn | 3270 | 2550 | 2510 | 2460 | 2970 |
| Mw | 8940 | 7140 | 5730 | 4950 | 5430 |
| acid # | 1.1 | 3.0 | 2.1 | 5.0 | 13 |
| amine # | 1.6 | 2.0 | 2.7 | 5.0 | 0.4 |
| softening pt., °C.[5] | 110 | 117 | 140 | 115 | 113 |
| Gardner color[6] | 6 | 5+ | 6 | 4 | 3 |
| clarity (4 wt. % in EtOH) | clear | clear | hazy | hazy | opaque |
| skin feel | fails | fails | N/A | N/A | N/A |

[1]Once-distilled dimer acid: ~80% dimer, 17% trimer acids.
[3]Sylfat ® FA-1 fatty acid is a product of Arizona Chemical.
[4]Equivalent ratio calculated from (DETA + HMDA equivs.)/(DETA + HMDA + EDA equivs) × 100, where DETA = diethylenetriamine, HMDA = hexamethylenediamine, and EDA = ethylenediamine.
[5]Ring and ball method, Mettler instrument, ASTM E28-99.
[6]50% solution in 1-propanol.

TABLE 3

Skin Feel Testing Results

| Resin | process | tightness | tack | oiliness | balls/flakes | skin feel |
|---|---|---|---|---|---|---|
| Trial 1: average score of five panelists | | | | | | |
| Polyamide A | RT | 1.2 | 1.2 | 1.8 | no | excellent |
| Polyamide B | RT | 1.4 | 1.6 | 2.6 | no | good |
| Polyamide C | RT | 1.8 | 1.6 | 3.2 | no | good |
| Polyamide D | hot | 1.0 | 1.0 | 1.4 | no | excellent |
| acrylates/octylacrylamide copolymer | RT | 2.0 | 1.4 | 2.0 | no | good |
| Trial 2: average score of six panelists | | | | | | |
| Polyamide A | RT | 1.3 | 1.7 | 2.2 | no | excellent |
| Polyamide D | hot | 1.8 | 2.2 | 2.3 | no | excellent |
| Polyamide L | RT | 1.5 | 1.8 | 2.8 | yes | unacceptable |
| acrylates/octylacrylamide copolymer | RT | 2.2 | 1.5 | 2.7 | no | good |

EXAMPLE 1

Ethanol-Based Sunscreen Spray (SPF 70): Room-Temperature Process

The indicated components for Phase A (see below) are combined in a vessel and heated with agitation to ~45° C. until the solid actives (avobenzone and benzophenone-3) dissolve and form a homogeneous solution. Phase A is then cooled to ~40° C. Separately, the Phase B components (30:70 hydrophobic polyamide/ethanol blend, ethanol, and glycerin) are combined and blended at room temperature. Phase A is then added to Phase B and blended with agitation to form a clear solution.

| Phase | Component | Wt. % |
|---|---|---|
| A | Homosalate | 15.0 |
|   | Benzophenone-3 | 6.0 |
|   | Ethylhexyl salicylate | 5.0 |
|   | Butyl methoxydibenzoylmethane (avobenzone) | 2.0 |
|   | Octocrylene | 2.0 |
| B | Glycerin | 2.0 |
|   | Hydrophobic polyamide/ethanol solution 30/70 | 13.3 |
|   | Ethanol SDA 40-B | 54.7 |
|   |   | 100.0 |

COMPARATIVE EXAMPLE 2

Ethanol-Based Sunscreen Spray (SPF 70) Based on Acrylic Film-Former

The procedure of Example 1 is used to make an ethanol-based sunscreen formulation except that acrylates/octylacrylamide copolymer (Dermacryl® 79, a product of AkzoNobel), a resin used in commercial sunscreen sprays, is used instead of the hydrophobic polyamide/ethanol blend. The formulation is shown below.

| Phase | Component | Wt. % |
|---|---|---|
| A | Homosalate | 15.0 |
|   | Benzophenone-3 | 6.0 |
|   | Ethylhexyl salicylate | 5.0 |
|   | Butyl methoxydibenzoylmethane | 2.0 |
|   | Octocrylene | 2.0 |
| B | Glycerin | 2.0 |
|   | acrylates/octylacrylamide copolymer | 4.0 |
|   | Ethanol SDA 40-B | 64.0 |
|   |   | 100.0 |

EXAMPLE 3

Ethanol-Based Sunscreen Spray (SFF 70): Hot Process

The indicated components for Phase A (see below) are combined in a vessel and heated with agitation to ~85° C. The solution is blended until the polyimide melts and blends into the organic active oil phase. Phase A is then cooled to ~40° C. Phase B, a mixture of ethanol and glycerin, is then added to Phase A, and the mixture is blended at room temperature until a clear, homogeneous solution results.

| Phase | Component | Wt. % |
|---|---|---|
| A | Homosalate | 15.0 |
|   | Benzophenone-3 | 6.0 |
|   | Ethylhexyl salicylate | 5.0 |
|   | Butyl methoxydibenzoylmethane | 2.0 |
|   | Octocrylene | 2.0 |
|   | Hydrophobic polyamide | 4.0 |
| B | Glycerin | 2.0 |
|   | Ethanol SDA 40-B | 64.0 |
|   |   | 100.0 |

EXAMPLE 4

Ethanol-Based Sunscreen Spray (SPF 70): One-Step Process

The indicated components (see below) are combined in a vessel and heated with agitation to ~60° C. The mixture is blended until the polyamide melts and the solid actives dissolve to form a clear solution. The blend is cooled to room temperature prior to discharge.

| Phase | Component | Wt. % |
|---|---|---|
| A | Homosalate | 15.0 |
|   | Benzophenone-3 | 6.0 |
|   | Ethylhexyl salicylate | 5.0 |
|   | Butyl methoxydibenzoylmethane | 2.0 |
|   | Octocrylene | 2.0 |
|   | Hydrophobic polyamide | 4.0 |
|   | Glycerin | 2.0 |
|   | Ethanol SDA 40-B | 64.0 |
|   |   | 100.0 |

EXAMPLE 5

Ethanol-Based Sunscreen Spray (100 SPF)

The procedure of Example 1 is used to combine the components shown below to make an SPF 100 ethanol-based continuous sunscreen spray.

| Phase | Component | Wt. % |
|---|---|---|
| A | Homosalate | 15.0 |
|   | Benzophenone-3 | 6.0 |
|   | Ethylhexyl salicylate | 5.0 |
|   | Butyl methoxydibenzoylmethane | 3.0 |
|   | Octocrylene | 10.0 |
| B | Glycerin | 2.0 |
|   | Hydrophobic polyamide/ethanol solution 30/70 | 13.3 |
|   | Ethanol SDA 40-B | 45.7 |
|   |   | 100.0 |

In Vitro SPF Testing

A nominal SPF 70 ethanol spray containing 4 wt. % resin is prepared from the film-forming resins listed in Table 4 below using either the room temperature process (see Example 1, above) or the hot process (see Example 3). Performance of the polyamide resins is compared with that of acrylates/octylacrylamide copolymer. A Labsphere 2000 transmittance analyzer is used to evaluate the SPF of the products. In each case, the polyamide resin provides satisfactory performance, comparable to that of the control acrylic resin (see Table 4). Additional in vitro tests using Polyamides E-H demonstrate good performance in the static SPF test (see Table 1).

TABLE 4

In Vitro SPF Results

| Resin | Process | SPF (mean) | std. dev. |
|---|---|---|---|
| acrylates/octylacrylamide copolymer | RT | 63 | 7.9 |
| Polyamide A | RT | 66 | 21 |
| Polyamide A | hot | 60 | 1.7 |
| Polyamide D | hot | 53 | 5.4 |

Water-Resistance Testing

Nominal SPF 70 ethanol sprays containing 4.0 wt. % resin are evaluated for water resistance. Comparative sprays include a acrylates/octylacrylamide copolymer-based spray, and a commercial product, Ocean Potion™ instant dry mist sunscreen (SPF 70). Test strips of 3M™ Transpore™ medical tape are attached to microscope slides, and the slides are weighed to the nearest 0.1 mg. About 60 mg of spray sample is applied to the slide, and the slide/tape/sample is allowed to air dry for 20 min. The slide is weighed accurately to determine the initial amount of applied sample. The slide is submerged in deionized water (100 g) at room temperature in an aluminum pan and allowed to stand for 80 min. The slide is removed from the water and dried in an oven at 45° C. overnight. Weight is again determined and the amount of weight loss is recorded. Three samples of each type are measured this way, and the average weight loss (%) is calculated. Results appear in Table 5. Additional in vitro tests using Polyamides F-H demonstrate good to excellent water resistance for these formulations (see Table 1).

TABLE 5

Water-Resistance Test Results

| | Wt. loss (%) after water immersion | | | |
|---|---|---|---|---|
| Resin | Sample 1 | Sample 2 | Sample 3 | Ave. Wt. Loss (%) |
| Ocean Potion | 48 | 47 | 44 | 46 |
| acrylates/ octylacrylamide copolymer | 33 | 37 | 40 | 37 |
| Polyamide A | 49 | 52 | 43 | 48 |
| Polyamide D | 40 | 50 | 49 | 46 |

The results indicate that the polyamide resins provide acceptable water resistance that is comparable to that afforded by an acrylates/octylacrylamide copolymer formulation and a commercial ethanol-based continuous spray sunscreen.

In Vivo Test Results

The performance of the SPF 70 formulations containing Polyamide A and acrylates/octylacrylamide copolymer is compared at an independent testing facility for 80-minute "very water resistant" (VWR) SPF testing. Each spray is evaluated on five test subjects over two days. No subjects are used for both formulations. Results appear in Table 6.

TABLE 6

In Vivo Tast Results: 80-Min. VWR SPF Values

| | SPF by Test Subject | | | | | Ave. SPF | Std. Dev. | Label SPF |
|---|---|---|---|---|---|---|---|---|
| | 1 | 2 | 3 | 4 | 5 | | | |
| Polyamide A | 70.0 | 60.9 | 80.5 | 77.6 | 70.0 | 71.8 | 35 | 69 |
| acrylates/ octylacrylamide copolymer | 92.4 | 80.5 | 60.9 | 70.0 | 80.5 | 76.9 | 11 | 72 |

The results indicate good performance of both SPF 70 ethanol-based sunscreen formulations with in vivo testing.

EXAMPLE 6

Fragrant Body Spray

The components shown below for Phase A are combined in a vessel and blended at room temperature to give a clear, homogeneous solution. The premixed Phase B components are then blended in with Phase A to form a clear solution useful as a fragrant body spray. The spray is stable at room temperature for 2 months.

| Phase | Component | Wt. % |
|---|---|---|
| A | Ethanol SDA 40-B | 72.8 |
| | Hydrophobic polyamide/ethanol solution 30/70 | 10.0 |
| | Glycerin | 4.0 |
| | Propylene glycol | 2.0 |
| | BHT | 0.2 |
| | Caprylyl methicone | 4.0 |
| B | Polysorbate 80 | 4.0 |
| | Fragrance | 3.0 |
| | | 100.0 |

EXAMPLE 7

Anti-Acne Spray

Ethanol SDA 40-B (59.0 wt %) is blended with hydrophobic polyamide/ethanol 30:70 solution (10.0 wt. %) at room temperature. Glycerin (12.5 wt. %) and DC 245 cyclopentasiloxane fluid (Dow Corning, 5.0 wt. %) are added to the polyamide solution and mixed until uniform. A solution of salicylic acid (2.0 wt. %) and ethanol SDA 40-B (10.0 wt. %) is added to the polyamide mixture and mixed until uniform. Finally, a solution of polysorbate 80 (1.0 wt. %) and fragrance (0.5 wt. %) is added and mixed until a homogeneous solution results. All amounts are based on 100 wt. % total.

EXAMPLE 8

Ethanol-Based Sunscreen Sprays: Effect of Polyamide Concentration on SPF and SPF Retention The procedure of Example 1 (room temperature process) is generally followed to produce nominal SPF 30 and SPF 50+ formulations containing 0 to 8 wt. % of Polyamide A. Thus, the indicated components for Phase A (see Table 7) are combined in a vessel and heated with agitation to ~45° C. until the solid actives (homosalate, benzophenone-3, avobenzone, ethylhexyl salicylate for the SPF 30 formulations; the same plus octocrylene for the SPF 50+ formulations) dissolve and form a homogeneous solution. Phase A is then cooled to ~40° C. Separately, the Phase B components (30:70 Polyamide A/ethanol blend, ethanol, and glycerin) are combined and blended at room temperature. Phase A is then added to Phase B and blended with agitation to form a clear solution.
In Vitro SPF Testing A Labsphere UV2000S transmittance analyzer is used to provide an instrumental approach to evaluate the SPF of the ethanol-based sunscreen sprays from transmittance/absorbance data of UV. Testing is performed on three samples for each of the ten formulations shown in Table 7 in accord with U.S. Food & Drug Administration (FDA) dry time and film weight standards, except that the samples are not pre-irradiated. A sample of sunscreen spray (22 µL) is pipetted onto a pre-weighed plate and is spread with a pre-saturated finger cot. This amount translates to a film weight of about 0.75 mg/cm$^2$ for the 25-cm$^2$ plate when the reduced density of ~0.85 g/cm$^3$ is taken into account. Samples are dried for 15 min., reweighed to determine film weight, and scanned in nine different locations (using the Labsphere 2000 analyzer) to get an initial SPF. The samples are then submerged for 80 min. in deionized water and air dried for 60 min. The samples are re-analyzed to obtain an 80-min. SPF value, and % SPF retention is calculated. Results appear in Table 7.

As shown in Table 7, increasing the concentration of Polyamide A generally enhances the SPF value. This attribute of the polyamide allows formulators to reduce the amount of sunscreen actives needed to achieve a desired SPF rating.

Figure 5:
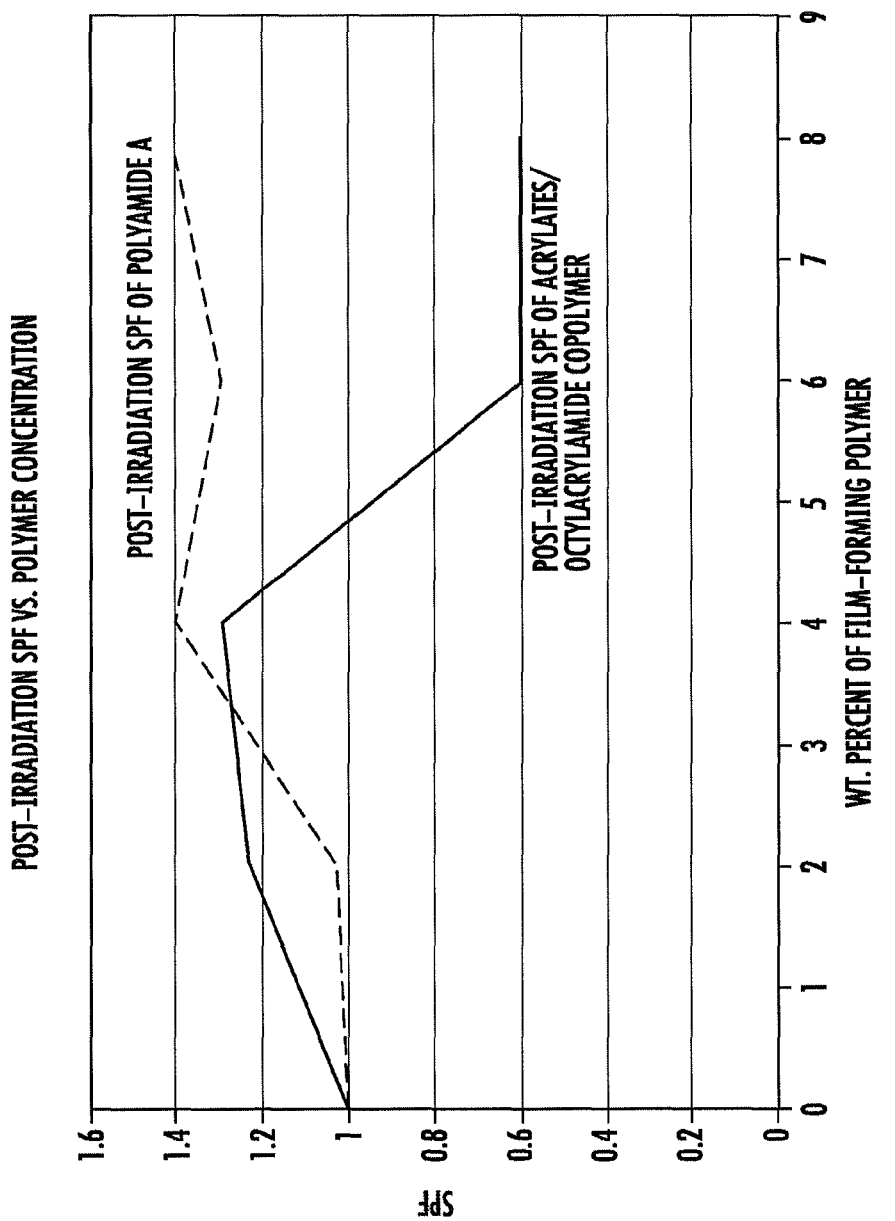
FIG. 5 plots SPF v. concentration in wt % of film-forming polymer added for a hydrophobic polyamide of the invention (Polyamide A) and an acrylates/octylacrylamide copolymer.

FIG. 5 shows the data of Tables 7a and 7b. This more dramatically points out a difference in behavior of SPF as a function of polymer concentration for a polyamide of this invention and an acrylates/octylacrylamide copolymer. The SPF value reported here is normalized for the in vitro method.

In this study, both polymers increase SPF of a sunscreen formulation when added in amounts up to 4 wt. %. However, above about 4 wt. % the SPF value begins to fall for the acrylates/octylacrylamide copolymer, while the polyamide retains its SPF boosting ability. This trend suggests that formulators will have more flexibility in the amount of polyamide used to deliver and hold sunscreen ingredients on the skin.

The current FDA testing protocol, which was originally designed to measure SPF in creams and lotions, is also used for ethanol-based sunscreen sprays. However, the quick drying nature and surface tension of ethanol-based sunscreens makes it difficult to produce an even film via this method. Adding a polymer to the formulation amplifies this difficulty. Thus, we noted poor spreadability at higher polymer loads (i.e., 6 or 8 wt. % for the SPF 30 blend, 8 wt. % for the SPF 50+ blend). The increased oil content of the SPF 50+ sunscreen enabled a spreadable system at a slightly higher polymer load.

Despite these limitations, increases in SPF are observed for both SPF 30 and SPF 50+ blends at low polymer loadings. For example, SPF increases up to 160% in the SPF 30 formulation (4 wt. % Polyamide A) and more than 250% in the SPF 50+ formulation (4 and 6 wt. % Polyamide A). Generally, the poorer SPF values at high polymer load can be attributed to poorer spreadability at these concentrations.

The water resistance of the control formulation is already high: the percent retention of SPF following 80-minute water immersion is 88% for the SPF 30 formulation and 53% for the SPF 50+ formulation. However, a slight increase in water resistance can be attributed to the presence of Polyamide A, particularly in the SPF 50+ formulations.
In Vitro Skin Tightening Study Ethanol-based sunscreen sprays (SPF 70) containing either Polyamide A or acrylates/octylacrylamide copolymer are applied to samples of VITRO-SKIN® (IMS, Inc., CT) a synthetic product having topography, pH, critical surface tension, and other properties resembling human skin. Skin tightening is evaluated using an Instron® instrument and measuring tightening force as a function of time. The formulation based on Polyamide A exhibits a reduced skin tightening effect when compared with an acrylates/octylacrylamide copolymer formulation in this test.

The method quantifies skin tightening qualities of a product by measuring forces of contraction or expansion of a skin substitute, mounted on a substrate support system. Contractile forces result from the nature of the film that is formed on the substrate. If a smooth film is formed that is compatible with all of the ingredients in the formula, the film exhibits less contraction on the skin. This manifests itself as giving a better skin feel. Because many evaporative and film formation processes are influenced by temperature, the equipment and substrate can be maintained at different temperatures during testing. This allows the skin tightening or relaxing effect of using different film-forming polymers for a skin care formulation to be compared.

TABLE 7a

SPF as a Function of wt % Polyamide A in a Sunscreen Formulation

| | Sample | | | | | | | | |
|---|---|---|---|---|---|---|---|---|---|
| | 0% Polyamide A (Control) | | | 2% Polyamide A | | | 4% Polyamide A | | |
| | | | | Plate # | | | | | |
| | 1 | 2 | 3 | 4 | 5 | 6 | 7 | 8 | 9 |
| Plate weight (g) | 7.287 | 7.295 | 7.3622 | 7.3667 | 7.3887 | 7.3051 | 7.4069 | 7.417 | 7.3606 |
| Sample volume (µL) | 22 | 22 | 22 | 22 | 22 | 22 | 22 | 22 | 22 |

TABLE 7a-continued

SPF as a Function of wt % Polyamide A in a Sunscreen Formulation

| | | | | | | | | | |
|---|---|---|---|---|---|---|---|---|---|
| Dry weight (g) | 7.291 | 7.2996 | 7.3678 | 7.3709 | 7.3935 | 7.3104 | 7.4124 | 7.4226 | 7.3666 |
| Film weight (g) | 0.004 | 0.0046 | 0.0056 | 0.0042 | 0.0048 | 0.0053 | 0.0055 | 0.0056 | 0.006 |
| Initial SPF (pre) | 10 | 13 | 12 | 9 | 11 | 16 | 16 | 16 | 15 |
| Average initial SPF | | 11.7 | | | 12.0 | | | 15.7 | |
| SPF StDev | | 1.5 | | | 3.6 | | | 0.6 | |
| Crit. wavelength (nm) | 375 | 375 | 375 | 374 | 374 | 374 | 374 | 374 | 374 |
| 4MED SPF (post) | 9 | 12 | 9 | 7 | 10 | 14 | 15 | 14 | 13 |
| Average SPF (post irradiation) | | 10.0 | | | 10.3 | | | 14.0 | |
| SPF StDev | | 1.7 | | | 3.5 | | | 1.0 | |
| Crit. wavelength (nm) | 374 | 374 | 374 | 373 | 374 | 374 | 374 | 373 | 373 |
| Average SPF loss | | 1.7 | | | 1.7 | | | 1.7 | |
| Average SPF loss | | 14.3 | | | 13.9 | | | 10.6 | |
| Percent SPF increase (post irradiation) | | 0 (Control) | | | 3% increase from 0% polymer concentration | | | 36% increase from 2% polymer concentration | |

| | | Sample | | | | | |
|---|---|---|---|---|---|---|---|
| | | 6% Polyamide A | | | 8% Polyamide A | | |
| | | Plate # | | | | | |
| | | 10 | 11 | 12 | 13 | 14 | 15 |
| Polyamide A | Plate weight (g) | 7.3703 | 7.3129 | 7.4097 | 7.3937 | 7.4036 | 7.4066 |
| | Sample volume (μL) | 22 | 22 | 22 | 22 | 22 | 22 |
| | Dry weight (g) | 7.3743 | 7.3175 | 7.4142 | 7.3983 | 7.4085 | 7.4124 |
| | Film weight (g) | 0.004 | 0.0046 | 0.0045 | 0.0046 | 0.0049 | 0.0058 |
| | Initial SPF (pre) | 16 | 13 | 14 | 17 | 13 | 15 |
| | Average initial SPF | | 14.3 | | | 15.0 | |
| | SPF StDev | | 1.5 | | | 2.0 | |
| | Crit. wavelength (nm) | 374 | 374 | 374 | 374 | 373 | 373 |
| | 4MED SPF (post) | 14 | 12 | 13 | 15 | 14 | 13 |
| | Average SPF (post irradiation) | | 13.0 | | | 14.0 | |
| | SPF StDev | | 1.0 | | | 1.0 | |
| | Crit. wavelength | 374 | 374 | 374 | 374 | 373 | 373 |
| | Average SPF loss | | 1.3 | | | 1.0 | |
| | Average SPF loss | | 9.3 | | | 6.7 | |
| | Percent SPF increase (post irradiation) | | 7.1% decrease from 4% polymer concentration | | | 7.7% increase from 6% polymer concentration | |

TABLE 7b

SPF as a Function of wt % Acrylates/Octylacrylamide Copolymer in a Sunscreen Formulation

| | | Sample | | | | | | | | |
|---|---|---|---|---|---|---|---|---|---|---|
| | | 0% acrylates/ octylacrylamide copolymer (Control) | | | 2% acrylates/ octylacrylamide copolymer | | | 4% acrylates/ octylacrylamide copolymer | | |
| | | Plate # | | | | | | | | |
| | | 1 | 2 | 3 | 4 | 5 | 6 | 7 | 8 | 9 |
| acrylates/ octylacrylamide copolymer | Plate weight (g) | 7.287 | 7.295 | 7.3622 | 7.3788 | 7.3545 | 7.3709 | 7.381 | 7.356 | 7.3583 |
| | Sample volume (μL) | 22 | 22 | 22 | 22 | 22 | 22 | 22 | 22 | 22 |
| | Dry weight (g) | 7.291 | 7.2996 | 7.3678 | 7.3808 | 7.3564 | 7.3748 | 7.3855 | 7.359 | 7.3639 |
| | Film weight (g) | 0.004 | 0.0046 | 0.0056 | 0.002 | 0.0019 | 0.0039 | 0.0045 | 0.003 | 0.0056 |
| | Initial SPF (pre) | 10 | 13 | 12 | 10 | 14 | 15 | 14 | 10 | 17 |
| | Average initial SPF | | 11.7 | | | 13.0 | | | 13.7 | |
| | SPF StDev | | 1.5 | | | 2.6 | | | 3.5 | |
| | Crit. wavelength (nm) | 375 | 375 | 375 | 374 | 374 | 374 | 374 | 374 | 374 |
| | 4MED SPF (post) | 9 | 12 | 9 | 10 | 13 | 14 | 13 | 10 | 16 |
| | Average SPF (post irradiation) | | 10.0 | | | 12.3 | | | 13.0 | |
| | SPF StDev | | 1.7 | | | 2.1 | | | 3.0 | |
| | Crit. wavelength (nm) | 374 | 374 | 374 | 373 | 373 | 373 | 373 | 374 | 373 |
| | Average SPF loss | | 1.7 | | | 0.7 | | | 0.7 | |
| | Average SPF loss | | 14.3 | | | 5.1 | | | 4.9 | |

TABLE 7b-continued

SPF as a Function of wt % Acrylates/Octylacrylamide Copolymer in a Sunscreen Formulation

| | 6% acrylates/octylacrylamide copolymer | | | 8% acrylates/octylacrylamide copolymer | | |
|---|---|---|---|---|---|---|
| Plate # | 10 | 11 | 12 | 13 | 14 | 15 |
| Plate weight (g) | 7.3654 | 7.3801 | 7.3942 | 7.3452 | 7.3964 | 7.3813 |
| Sample volume (µL) | 22 | 22 | 22 | 22 | 22 | 22 |
| Dry weight (g) | 7.3685 | 7.3831 | 7.3997 | 7.3495 | 7.4008 | 7.3856 |
| Film weight (g) | 0.0031 | 0.003 | 0.0055 | 0.0043 | 0.0044 | 0.0043 |
| Initial SPF (pre) | 6 | 5 | 9 | 7 | 5 | 6 |
| Average initial SPF | | 6.7 | | | 6.0 | |
| SPF StDev | | 2.1 | | | 1.0 | |
| Crit. wavelength (nm) | 376 | 377 | 375 | 375 | 376 | 377 |
| 4MED SPF (post) | 5 | 4 | 9 | 7 | 5 | 6 |
| Average SPF (post irradiation) | | 6.0 | | | 6.0 | |
| SPF StDev | | 2.6 | | | 1.0 | |
| Crit. wavelength (nm) | 375 | 376 | 375 | 374 | 375 | 376 |
| Average SPF loss | | 0.7 | | | 0.0 | |
| Average SPF loss | | 10.0 | | | 0.0 | |
| | | 54% decrease from 4% polymer concentration | | | 0% decrease from 6% polymer concentration | |

Testing for skin tightening begins with a strip of the synthetic skin (9.5 cm×2.0 cm) looped over the support bars as shown in FIG. 1. giving an effective horizontal substrate area of 2.5 cm×2.0 cm. The substrate is stretched to put the sample in tension, to give an initial load cell output of about 30-40 g. The sample is held at this force until the readout is stable. A known amount of sunscreen spray is then applied uniformly to the horizontal section of the substrate, and the load cell output is recorded as a function of time. An increase in contractile force indicates film formation and substrate contraction ("skin tightening").

FIG. 1 depicts a substrate support system attached to a load cell (1) of a force-measuring machine, such as an Instron® tester. A clamp (2) suitable for retaining an artificial skin sample substrate (3) is attached to the load cell. The substrate extends downward and is drawn under and over first and second bars (4), respectively, to form a horizontal testing region. The substrate extends downward from the second bar to a lower clamp (5) and then to a stationary clamp (6). Heating block (7) is used to control temperature in the testing region, and a thermocouple (8) and temperature controller (9) are included. The Instron® cross-head (10) is also shown.

Figure 2:
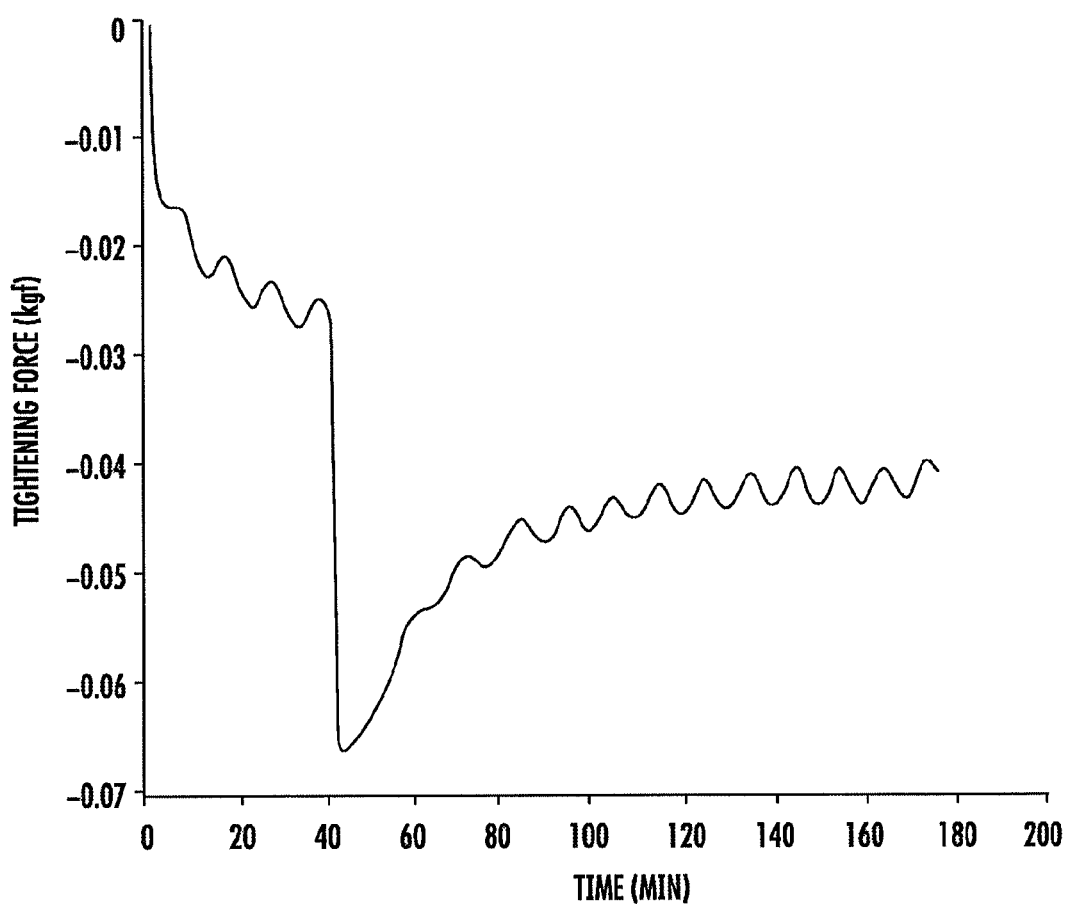
FIG. 2 plots contractile force v. time for a skin-tightening control sample.

To ensure that the method can identify small changes in akin tightening, a commercial skin-firming lotion (CVS antiwrinkle and skin tightening lotion) is used as a positive control. FIG. 2 shows the curve for a load cell output as a function of time before and after product application. This skin-firming control demonstrates an increase in the output force of the load cell as a function of time, which reflects skin tightening. Initially, because of water and/or humectants in the skintightening product, the sample expands. Once the sample equilibrates, however, the output force increases as the skin begins to tighten.

A 1.5-cm width of VITRO-SKIN® is mounted as depicted in FIG. 1. Initially a small tension is applied to create a small load cell output. When this force levels off after relaxation of the skin, the sunscreen spray (four drops, about 200 µL) is applied. The Instron® cross-head is moved down to stretch the skin, and output from the load cell is monitored for up to 180 min. Initially, there is a decrease in the load cell output (from wetting of the VITRO-SKIN®), followed by an increase as the skin tightens.

Figure 3:
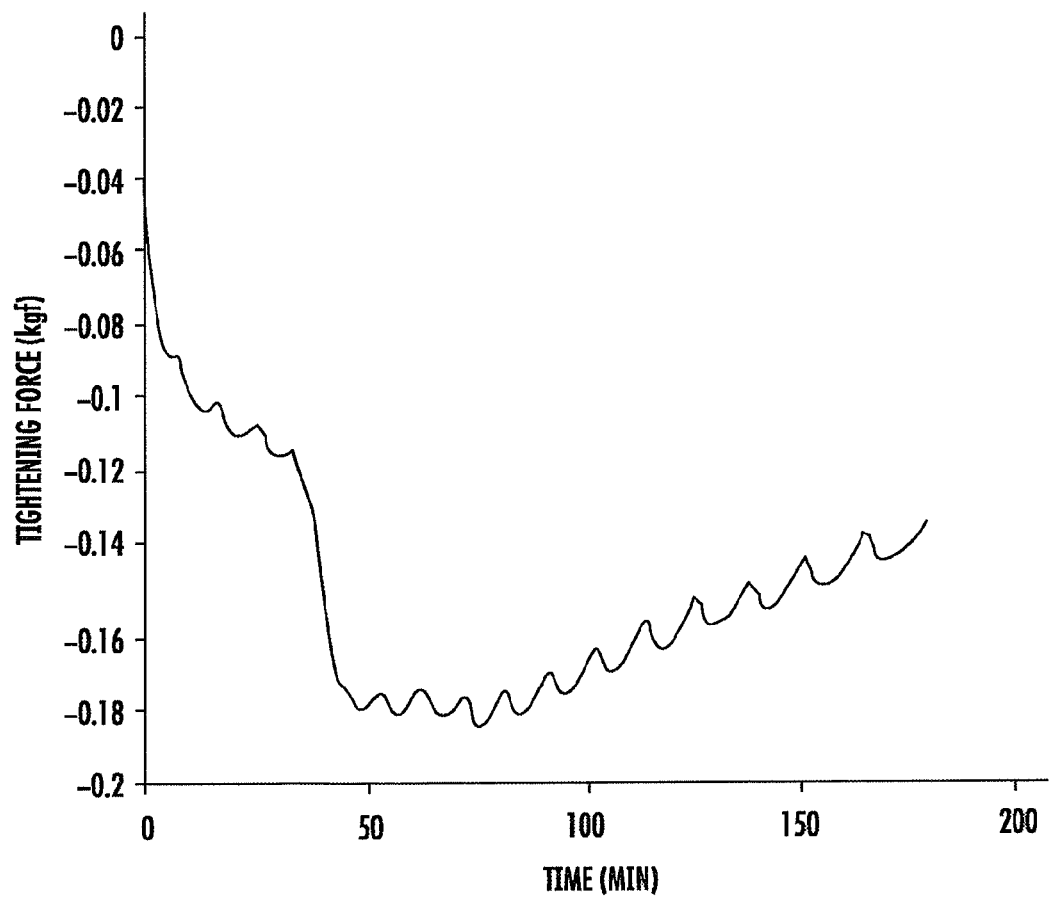
FIG. 3 plots contractile force v. time for a skin sample treated with an ethanol-based SPF 70 sunscreen spray containing acrylates/octylacrylamide copolymer, a commercial film-forming agent.
Figure 4:
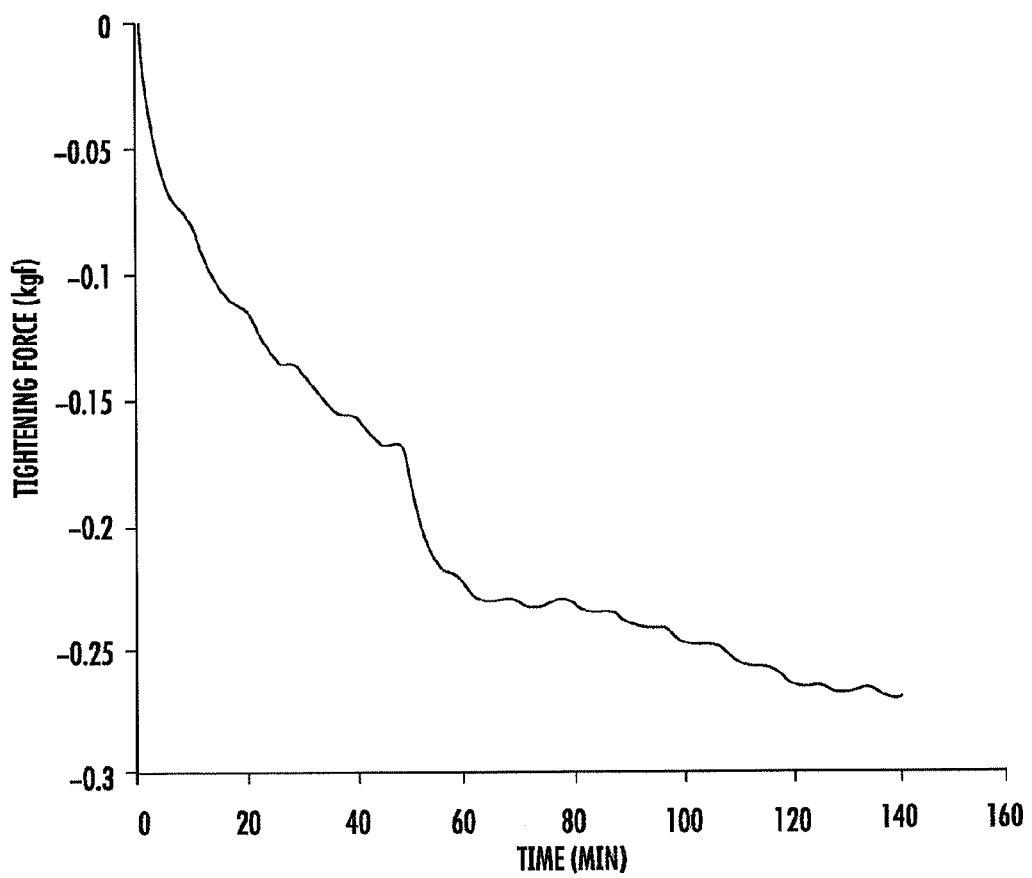
FIG. 4 plots contractile force v. time for a skin sample treated with an ethanol-based SPF-70 sunscreen spray containing Polyamide A.

The SPF 70 sunscreen formulations described in Example 1 and Comparative Example 2, which contain 4 wt. % of either acrylates/octylacrylamide copolymer or Polyamide A, are tested under identical conditions at 25° C., and data obtained from the experiments is shown in FIGS. 3 and 4, respectively.

FIG. 3 plots contractile force v. time for a skin sample treated with an ethanol-based SPF 70 sunscreen spray containing acrylates/octylacrylamide copolymer, a commercial film-forming agent.

FIG. 4 plots contractile force v. time for a skin sample treated with an ethanol-based SPF-70 sunscreen spray containing Polyamide A.

The sample treated with an ethanol spray formulation containing acrylates/octylacrylamide copolymer exhibits higher skin tightening than the formulation based on Polyamide A. The results mirror the skin panel test results for the SPF 70 formulations.

We surprisingly found that hydrophobic polyamides can be formulated into a finished ethanol-based continuous sunscreen spray, without the need to neat the polyamide or an ethanol-polyamide mixture. Methods of mixing such compositions are shown in Examples 9 and 10 below.

EXAMPLE 9

Room-Temperature Addition of Hydrophobic Polyamide to a Finished Continuous Spray Sunscreen The sunscreen active components of Phase A (homosalate, benzophenone-3, ethylhexyl salicylate, avobenzone, and octocrylene) in the amounts shown in Table 8 are warmed to 40° C. under gentle agitation to give a homogeneous mixture, then allowed to cool to room temperature. Phase B components (glycerin and ethanol) are premixed at room temperature and then combined with the Phase A mixture. Polyamide A is then added to the blend at room temperature while stirring at about 500 rpm. A homogeneous mixture is obtained after 30-40 minutes of stirring at room temperature (see Table 8 for results). The sprayable formulation is non-tacky and non-oily.

EXAMPLE 10

The procedure of Example 9 is generally followed to make an SPF 50+ formulation, except that 6.0 wt. % of benzophenone-3 and 64 wt % of ethanol SDA 40-B are used. Dissolution of Polyamide A is complete in about 30 min. at room temperature. The sprayable formulation is non-tacky and non-oily. In vivo testing (80 min. VWR protocol) results in a mean SPF of 72±7.

TABLE 8

Continuous Spray Sunscreens
Room-Temperature Preparation

|  | SPF 35 Formulations (wt. %) | | SPF 50+ Formulations (wt. %) | |
| --- | --- | --- | --- | --- |
| Phase A[1] | | | | |
| Homosalate | 15.0 | | 15.0 | |
| Benzophenone-3 | 4.0 | | 4.0 | |
| Ethylhexyl salicylate | 5.0 | | 5.0 | |
| Avobenzone | 2.0 | | 2.0 | |
| Octocrylene | 0 | | 2.0 | |
| Phase B | | | | |
| Glycerin | 2 | 2 | 2 | 2 |
| Ethanol SDA 40-B | 70 | 68 | 68 | 66 |
| Phase C | | | | |
| Polyamide A | 2.0 | 2.0 | 4.0 | 4.0 |
| Phase C dissolution time (min) at room temperature | 35 | 33 | 33 | <40 |

[1]Sunscreen filters are heated to 40° C. with gentle mixing and then cooled to room temperature.

EXAMPLE 11

Use of Fatty Alcohols to Compatibilize Ethanol/Polyamide Blends at Room Temperature Polyamide A (7.0 wt. %, pastilles) and 2-octyldodecanol (7.0 wt. %) are combined under ambient conditions with ethanol SDA 40-B (86 wt. %). After stirring for 35 min. at room temperature, a clear solution results.

The procedure is repeated with Polyamide A (7.3 wt. %, in pastille form), 2-octyldodecanol (3.6 wt. %), and ethanol SDA 40-B (89 wt. %). A clear solution results after stirring 38 min. at room temperature.

Polyamide A pastilles are ground to granules using a mortar and pestle.

The procedure is repeated with Polyamide A (6.9 wt. %, granules), 2-octyldodecanol (6.9 wt. %), and ethanol SDA 40-B (86.2 wt. %). A clear solution results after stirring 17 min. at room temperature.

The procedure is repeated with Polyamide A (7.1 wt. %, granules), 2-octyldodecanol (3.6 wt. %), and ethanol SDA 40-B (89.3 wt. %). A clear solution results after stirring 10 min. at room temperature.

Similar experiments are performed using granulated Polyamide A and isostearyl alcohol, oleyl alcohol, castor oil, or ethylhexyl glycerin instead of 2-octyldodecanol. In each case, a homogeneous solution results within about 20 minutes of stirring at room temperature.

COMPARATIVE EXAMPLE 12

The procedure of Example 11 is repeated with Polyamide A (7.4 wt. %, granules) and ethanol SDA 40-B (92.6%) only. Thus, no 2-octyldodecanol is used. The solution remains slightly cloudy after mixing for 24 hours at room temperature.

The procedure of Example 11 is repeated with Polyamide A granules (7.3 wt. %), ethanol SDA 40-B (91.7 wt. %), and 2-octyldodecanol (1.0 wt. %). The solution remains slightly cloudy after mixing for 24 hours at room temperature.

Example 11 and comparative Example 12 show that fatty alcohols can be used to compatibilize the mixtures of ethanol and hydrophobic polyamides that are useful in continuous sunscreen sprays.

EXAMPLE 13

Long-Lasting Fragrant Body Lotion from Polyamide A

Carbopol® Ultrez 21, an acrylates/$C_{10}$-$C_{30}$ alkyl acrylate crosspolymer (0.25 g, product of Lubrizol), is dispersed in water (72.2 g) and mixed about 20 min. until uniform. Disodium EDTA (0.05 g) and triethanolamine (1.0 g) are added, and the mixture is heated to 70-80° C. to give Phase A. Separately, Phase B is prepared as follows. Polyamide A (2.0 g) is combined and mixed with 2-octyldodecanol (3.0 g) at 75° C. to 85° C. (see note below). The remaining Phase B components are then added. Thus, stearic acid (2.0 g), glyceryl stearate (2.0 g), benzyl alcohol (0.5 g), 2-ethylhexyl glycerin (4.0 g), dimethicone (4.0 g), tocopherol (0.2 g), aloe oil extract (0.2 g), black mulberry leaf extract (0.3 g), isononyl isononanoate (2.0 g), and caprylic/capric triglyceride (3.0 g) are added, and the Phase B components are heated to 75° C. and mixed until homogeneous. Phase B is then added to Phase A, and the resulting mixture is cooled while mixing to 60° C. The mixture is further cooled to room temperature under sweep agitation. Fragrance (3.0 g) is added, followed by Phenonip® 2-phenoxyethanol/parabens mixture (0.3 g, product of Clariant).

The resulting homogeneous emulsion is stable for 2 months at room temperature, 1.5 months at 40° C., and 1 week at 50° C. The emulsion is freeze-thaw stable through three cycles, and is thick enough to resist dripping when held vertically. 24-h Brookfield viscosity: 15,000-18,000 cP (Spindle #5, 20 rpm, 20° C. 1 min); pH=7.0-8.0.

Note: Polyamide A is incorporated into Phase B at much lower temperatures when combined with 2-octyldodecanol first; otherwise, the mixtures needs to be heated to ~125° C. This comment also applies to Example 14, below.

EXAMPLE 14

Sport Sunscreen Lotion: SPF 50

Pemulen™ TR-1 polymeric emulsifier (acrylates/C10-30 alkyl acrylate crosspolymer, product of Lubrizol, 0.38 g) is slowly added to water (49.21 g) and mixed at high speed for about 20 min. until homogeneous. Propylene glycol (5.0 g), disodium EDTA (0.050 g), benzyl alcohol (0.50 g), and chlorphenesin (0.30 g) are added, and the mixture is heated to 80° C. and stirred until homogeneous to complete Phase A. Separately, Phase B is prepared as follows. Polyamide A (2.0 g) is combined and mixed with 2-octyldodecanol (5.0 g) at 75° C. to 85° C. The remaining Phase B components are then added. Thus, avobenzone (3.0 g), homosalate (13.0 g), 2-ethylhexyl salicylate (5.0 g), octocrylene (5.0 g), benzophenone-3 (6.0 g), tocopherol (0.010 g), and oleth-3 (0.20 g) are added, and the Phase B mixture is heated and stirred at 80-85° C. until homogeneous. Phase B is added to Phase A over 3 min. while both mixtures are at 80-85° C. under high-speed agitation. The mixture is homogenized for 2-4 min. while avoiding aeration. The mixture is allowed to cool to 50° C. using sweep mixing. Phase C, a mixture of triethanolamine (0.35 g) in water (5.0 g), is added, and viscosity increases. Sweep mixing continues at room temperature until the mixture is homogeneous.

The resulting viscous, white lotion is stable for 2 months at room temperature, 1.5 months at 40° C., and 1 week at 50° C. 24-h Brookfield viscosity: 15,000 to 20,000 cP (Spindle #5, 20 rpm, 1 min.); pH; 5.5-6.5. Results of in vitro SPF and SPF retention after 80 min. water immersion appear in Table 9. Results of in vivo testing, performed as described earlier, appear in Table 10.

COMPARATIVE EXAMPLE 15

The procedure of Example 14 is repeated except that Polyamide A is omitted from Phase B, and Phase C uses 7.0 g of water.

The resulting viscous, white lotion is stable for 2 months at room temperature and 45° C. 24-h Brookfield viscosity: 15,000 to 20,00 cP (Spindle #5, 20 rpm, 1 min.); pH: 5.5-6.5. Results of in vitro SPF and SPF retention after 80 min. water immersion, performed as described earlier, appear in Table 9. Results of in vivo testing, performed as described earlier, appear in Table 10.

In Vitro SPF Testing

A Labsphere 2000 transmittance analyzer is used to evaluate the SPF of the sunscreen lotions prepared in Example 14 and Comparative Example 15. A 21-mg sample of sunscreen is applied to a 5-cm square PMMA plate. The sample is allowed to dry for 20 min. prior to scanning. The Labsphere analyzer is used to scan each plate in 9 different locations, and each sample is run in triplicate. The initial SPF values are recorded. The samples are then submerged for 80 min. in deionized water and air dried for 60 min. The samples are re-analyzed to obtain an 80-min. SPF value. Results appear in Table 9.

TABLE 9

In Vitro SPF Results: SPF 50 Lotions

| Example | SPF, 0 min., ave | std. dev. | SPF, 80 min., ave | std. dev. |
|---|---|---|---|---|
| 14 | 56 | 5.0 | 35 | 3.5 |
| C15 | 43 | 6.2 | 33 | 2.1 |

As the results in Table 9 indicate, static SPF of sunscreen lotions is enhanced by the presence of Polyamide A, while the results after water immersion are comparable to the control.

In Vivo Test Results

The performance of the SPF 50 lotions with and without Polyamide A is compared at an independent testing facility for 80-minute "very water resistant" (VWR) SPF testing. Each lotion is evaluated on five test subjects over two days. No subjects are used for both formulations. Results appear in Table 10.

TABLE 10

In Vivo Test Results: SPF 50 Lotions

| Example | 1 | 2 | 3 | 4 | 5 | Label SPF |
|---|---|---|---|---|---|---|
| | Static SPF by Test Subject | | | | | |
| 14 | 50.0 | 57.5 | 57.5 | 66.1 | 57.5 | 54 |
| C15 | <40 | 43.5 | 50.0 | 57.5 | <40 | 47* |
| | 80-min VWR SPF by Test Subject | | | | | |
| 14 | 43.5 | 43.5 | 57.5 | 57.5 | 57.5 | 47 |
| C15 | <40 | <40 | <40 | 50.0 | <40 | — |

*Ave. of 3 best results. SPF values <40 indicate a failed test.

The results in Table 10 show that the benefits for static SPF seen earlier extend to testing with live subjects. Inclusion of Polyamide A at 2 wt % improves static SPF. In contrast to the in vitro results, however, in vivo testing shows that much better water resistance is achieved when Polyamide A is included in the formulation. All five subjects pass the 80-min. VWR test when Polyamide A is present, versus only one of five passing without Polyamide A in the lotion. The results are impressive when taking into account how easily emulsions tend to wash off the skin.

Gel Point Recovery Data

Certain inventive compositions may have improved gel resistance and allow for solution recovery at ambient temperatures. Upon storage, particularly at low temperatures, solutions of polyamides in ethanol (such as the 30% solids in ethanol solutions commonly used in the industry) can develop gels. Ideally, the temperature at which gels form is as low as possible. Additionally, "gel recovery," i.e., reversion of the gel to liquid form, preferably occurs under ambient conditions. i.e., without heating the mixture above room temperature. Thus, phase separation in a stored container ideally resolves itself when the ambient conditions warm to more normal temperatures.

Table 11 provides gel recovery data for selected hydrophobic polyamides. As shown in the table. Polyamides G and H offer the lowest gel formation temperatures (15.6° C.) and relatively rapid recovery from gel to liquid at room temperature.

TABLE 11

Gel Point Recovery for Polyamide/Ethanol Blends

| | Polyamide | | | | | |
|---|---|---|---|---|---|---|
| | E | F | G | H | J | K |
| Gel formation temp, ° C. | 18.3 | 18.3 | 15.6 | 15.6 | 18.3 | 18.3 |
| Gel recovery at RT | no | no | yes | yes | no | no |
| drop time, min. | — | — | 38 | 37 | — | — |
| full recovery time, min. | — | — | 55 | 54 | — | — |
| Recovery temp. required, ° C. | 30-35 | 30-35 | RT | RT | — | — |

RT = room temperature

The preceding examples are meant only as illustrations. The following claims define the invention.

We claim:

1. A clear, film-forming concentrate, suitable for use in personal care products, comprising 50 to 99.9 wt. % of ethanol and 0.1 to 50 wt. % of a hydrophobic polyamide, wherein the polyamide comprises either:
   (a) a reaction product of a group of reactants, said group consisting of a dimerized fatty acid, acetic acid, propionic acid, and a polyamine component comprising ethylenediamine and 1 to 30 eq. % of one or more di- or triamines; or (b) a reaction product of a dimerized fatty acid, at least 50 wt. % of a $C_{16}$-$C_{22}$ unsaturated carboxylic acid, and at least one $C_2$-$C_6$ diamine;

wherein the polyamide has a number average molecular weight within the range of 1000 to 5000, an acid number less than 10 mg KOH/g, and an amine number less than 5 mg KOH/g.

2. The concentrate of claim 1 comprising 90 to 99 wt. % of ethanol and 1 to 10 wt. % of the polyamide.

3. The concentrate of claim 1 wherein the polyamide comprises (b) and the $C_2$-$C_6$ diamine is hexamethylene diamine.

4. The concentrate of claim 1 wherein the polyamide comprises (b) and the $C_{16}$-$C_{22}$ unsaturated carboxylic acid is oleic acid.

5. The concentrate of claim 1 wherein the polyamide is a reaction product of 25 to 35 wt. % of the dimerized fatty acid, 55 to 55 wt. % of the $C_{16}$-$C_{22}$ unsaturated carboxylic acid, and 9 to 10 wt. % of ethylenediamine.

6. The concentrate of claim 1 wherein the polyamide, when mixed with 200 proof ethanol, exhibits a cloud point, if any, below 15 wt. % polyamide.

7. The concentrate of claim 1 further comprising a sunscreen active component.

8. A continuous sunscreen spray having improved skin feel, comprising at least one sunscreen active component and the concentrate of claim 1.

9. The sunscreen spray of claim 8 further comprising glycerin.

10. The sunscreen spray of claim 8 comprising 0.2 to 8 wt. % of the polyamide.

11. A body spray or splash comprising a fragrance and the concentrate of claim 1.

12. A spray comprising the concentrate of claim 1 and at least one topical medication, anti-itch agent, hair-growth stimulant, hair styling agent, hair conditioner, skin toner, antiseptic, deodorant, antiperspirant, or moisturizer.

13. A film-forming concentrate, suitable for use in coating fabrics, comprising 50 to 99.9 wt. % of ethanol and 0.1 to 50 wt. % of a hydrophobic polyamide, wherein the polyamide comprises:
(a) a reaction product of a group of reactants, said group consisting of a dimerized fatty acid, acetic acid, propionic acid, and a polyamine component comprising ethylenediamine and 1 to 30 eq. % of one or more di- or triamines; or
(b) a reaction product of a dimerized fatty acid, at least 50 wt. % of a $C_{16}$-$C_{22}$ unsaturated carboxylic acid, and at least one $C_2$-$C_6$ diamine;
wherein the polyamide has a number average molecular weight within the range of 1000 to 5000, an acid number less than 10 mg KOH/g, and an amine number less than 5 mg KOH/g.

14. The concentrate of claim 13 further comprising an active material selected from the group consisting of insecticides, water repellants, stain repellants, disinfectants, deodorizers, antistatic agents, and mixtures thereof.

15. A method for making a continuous sunscreen spray, comprising:
(a) combining one or more sunscreen actives with ethanol at a temperature within the range of 20° C. to 50° C. to form a first mixture; and
(b) combining the first mixture with a hydrophobic polyamide at a temperature within the range of 15° C. to 40° C. to give the continuous sunscreen spray wherein the polyamide comprises either: (a) a reaction product of a group of reactants, said group consisting of a dimerized fatty acid, acetic acid, propionic acid, and a polyamine component comprising ethylenediamine and 1 to 30 eq. % of one or more di- or triamines; or (b) a reaction product of a dimerized fatty acid, at least 50 wt. % of a $C_{16}$-$C_{22}$ unsaturated carboxylic acid, and at least one $C_2$-$C_6$ diamine; wherein the polyamide has a number average molecular weight within the range of 1000 to 5000, an acid number less than 10 mg KOH/g, and an amine number less than 5 mg KOH/g.

16. The method of claim 15 wherein at least step (b) is performed at room temperature.

17. The method of claim 15 wherein the first mixture further comprises glycerin.

18. The method of claim 15 wherein the spray further comprises a fatty alcohol.

19. The method of claim 15 wherein the spray comprises two or more sunscreen actives, and the sunscreen actives are combined prior to step (a).

20. A method for making a continuous sunscreen spray, comprising combining a hydrophobic polyamide with ethanol and at least one sunscreen active in the presence of at least 2 wt. %, based on the amount of sunscreen spray, of a fatty alcohol; wherein the polyamide comprises either: (a) a reaction product of a group of reactants, said group consisting of a dimerized fatty acid, acetic acid, propionic acid, and a polyamine component comprising ethylenediamine and 1 to 30 eq. % of one or more di- or triamines; or (b) a reaction product of a dimerized fatty acid, at least 50 wt. % of a $C_{16}$-$C_{22}$ unsaturated carboxylic acid, and at least one $C_2$-$C_6$ diamine; wherein the polyamide has a number average molecular weight within the range of 1000 to 5000, an acid number less than 10 mg KOH/g, and an amine number less than 5 mg KOH/g.

21. The method of claim 20 wherein the fatty alcohol is selected from the group consisting of 2-octyldodecanol, oleyl alcohol, castor oil, isostearyl alcohol, 2-ethylhexyl glycerin, and mixtures thereof.

22. The method of claim 20 wherein the fatty alcohol is 2-octyldodecanol.

23. The method of claim 20 wherein the fatty alcohol is used in an amount within the range of 2 to 8 wt. % based on the amount of sunscreen spray.

24. An oil-in-water emulsion comprising:
(a) a continuous phase comprising 30 to 90 wt. %, based on the amount of emulsion, of water; and
(b) a discontinuous phase comprising at least one oil component and a hydrophobic polyamide, wherein the polyamide comprises:
(i) a reaction product of a group of reactants, said group consisting of a dimerized fatty acid, acetic acid, propionic acid, and a polyamine component comprising ethylenediamine and 1 to 30 eq. % of one or more di- or triamines; or
(ii) a reaction product of a dimerized fatty acid, at least 50 wt. % of a $C_{16}$-$C_{22}$ unsaturated carboxylic acid, and at least one $C_2$-$C_6$ diamine; wherein the polyamide has a number average molecular weight within the range of 1000 to 5000, an acid number less than 10 mg KOH/g, and an amine number less than 5 mg KOH/g.

25. The emulsion of claim 24 wherein the oil component comprises at least one sunscreen active.

26. The emulsion of claim 25 having a stability of at least 2 months at room temperature.

27. A fragrant body lotion comprising the emulsion of claim 24.

28. A sunscreen lotion comprising the emulsion of claim 24.

29. A water-in-oil emulsion comprising:
(a) a discontinuous phase comprising water; and
(b) a continuous phase comprising at least one oil component and a hydrophobic polyamide, wherein the polyamide comprises:
(i) a reaction product of a group of reactants, said group consisting of a dimerized fatty acid, acetic acid, propionic acid, and a polyamine component comprising ethylenediamine and 1 to 30 eq. % of one or more di- or triamines; or
(ii) a reaction product of a dimerized fatty acid, at least 50 wt. % of a $C_{16}$-$C_{22}$ unsaturated carboxylic acid, and at least one $C_2$-$C_6$ diamine; wherein the polyamide has a number average molecular weight within the range of 1000 to 5000, an acid number less than 10 mg KOH/g, and an amine number less than 5 mg KOH/g.

* * * * *